(12) United States Patent
Singh et al.

(10) Patent No.: US 7,482,351 B2
(45) Date of Patent: Jan. 27, 2009

(54) 4-PYRIMIDINEAMINE COMPOUNDS AND THEIR USES AS ANTI-PROLIFERATIVE AGENTS

(75) Inventors: Rajinder Singh, Belmont, CA (US); Ankush Argade, Foster City, CA (US); David Carroll, San Francisco, CA (US); Tarikere Gururaja, Santa Clara, CA (US); Taisei Kinoshita, San Mateo, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 317 days.

(21) Appl. No.: 11/171,970

(22) Filed: Jun. 29, 2005

(65) Prior Publication Data

US 2006/0040955 A1    Feb. 23, 2006

Related U.S. Application Data

(60) Provisional application No. 60/584,373, filed on Jun. 29, 2004.

(51) Int. Cl.
*A01N 43/54* (2006.01)
*C07D 239/42* (2006.01)
*C07D 401/04* (2006.01)
*C07D 239/02* (2006.01)

(52) U.S. Cl. ..................... 514/256; 544/326
(58) Field of Classification Search ........... None
See application file for complete search history.

(56) References Cited

U.S. PATENT DOCUMENTS

2007/0167439 A1 * 7/2007 Singh et al. ............ 514/224.2

FOREIGN PATENT DOCUMENTS

DE    40 29 649    3/1992
WO    WO 03/030909    4/2003
WO    WO 2004/046118    6/2004
WO    WO 2005/012294    2/2005

OTHER PUBLICATIONS

Chawla et. al.; CRIPS vol. 5, No. I, p. 9-12.*
Vippagunta et. al.; 2007; Crystalline Solids; 3.4 Prediction of the formation of hydrates and solvates, p. 1-26; p. 18.*
Lipinski et. al.; Annual Reoprts in Medicinal Chemistry; 1986; vol. 21 p. 283-291.*
Patani et. al.; Chemical Reviews; 1996; vol. 96 p. 3147-3176.*
Byrn et al., "Solid State analysis of the active pharmaceutical ingredient in drug products", 2003, Drug Discovery Today, vol. 8, No. 19, 898-905.*
Jantzen et. al.; 1996; "B. Prodrugs"; p. 596; Modern Pharmaceuticals; Marcel Dekker Inc.*
Cecil Textbook of Medicine, 21st Edition (2000), Goldman & Bennett (Editors), W.B. Saunders Company (Publisher), Chapter 198, pp. 1060-1074).*
PCT International Search Report, Nov. 21, 2005.
S.K. Robev, "Synthesis of 3-(2-Aryl-4-Arylamino-5-Pyrimidly)-1,2,4-Triazoles," 1983, *Tome*, 36(3): 353-356.
Yurugi et al., "Studies on the Synthesis of N-Heterocyclic Compounds," 1971 *Chem. Pharm. Bull.*, 19(11): 2354-2364.
S.K. Robev, "On the Reaction of Some Amidrazones in the Pyrimidine Series with Carbonyl Compounds," 1983, Tome 36(10): 1315-1318.
Ruderf et al., "Acylformylketene Acetals: Versatile Synthons for the Synthesis of Isoxazoles, Pyrazoles and Pyrimidines," 1993, *Sulfur Letters*, 16(2): 77-89.

* cited by examiner

*Primary Examiner*—Bruck Kifle
*Assistant Examiner*—Jeffrey H Murray
(74) *Attorney, Agent, or Firm*—McDonnell Boehnen Hulbert & Berghoff LLP

(57) ABSTRACT

The present disclosure provides 4-pyrimidineamine compounds having antiproliferative activity, compositions comprising the compounds and methods of using the compounds to inhibit cellular proliferation and to treat proliferative diseases such as tumorigenic cancers.

20 Claims, No Drawings

4-PYRIMIDINEAMINE COMPOUNDS AND THEIR USES AS ANTI-PROLIFERATIVE AGENTS

1. FIELD

The present disclosure relates to 4-pyrimidineamine compounds that exhibit antiproliferative activity, pharmaceutical compositions comprising the compounds and the use of the compounds in a variety of contexts, including for the treatment of proliferative disorders, such as, for example, tumors and cancers.

2. BACKGROUND

Cancer is a group of varied diseases characterized by uncontrolled growth and spread of abnormal cells. Generally, all types of cancers involve some abnormality in the control of cell growth and division. The pathways regulating cell division and/or cellular communication become altered in cancer cells such that the effects of these regulatory mechanisms in controlling and limiting cell growth fails or is bypassed. Through successive rounds of mutation and natural selection, a group of abnormal cells, generally originating from a single mutant cell, accumulates additional mutations that provide selective growth advantage over other cells, and thus evolves into a cell type that predominates in the cell mass. This process of mutation and natural selection is enhanced by genetic instability displayed by many types of cancer cells, an instability which is either gained from somatic mutations or by inheritance from the germ line. The enhanced mutability of cancerous cells increases the probability of their progression towards formation of malignant cells. As the cancer cells further evolve, some become locally invasive and then metastasize to colonize tissues other than the cancer cell's tissue of origin. This property along with the heterogeneity of the tumor cell population makes cancer a particularly difficult disease to treat and eradicate.

Traditional cancer treatments take advantage of the higher proliferative capacity of cancer cells and their increased sensitivity to DNA damage. Ionizing radiation, including γ-rays and x-rays, and cytotoxic agents, such as bleomycin, cisplatin, vinblastine, cyclophosphamide, 5'-fluorouracil, and methotrexate rely upon a generalized damage to DNA and destabilization of chromosomal structure which eventually lead to destruction of cancer cells. These treatments are particularly effective for those types of cancers that have defects in cell cycle checkpoints, which limits the ability of these cells to repair damaged DNA before undergoing additional cell division. The non-selective nature of these treatments, however, often results in severe and debilitating side effects. The systemic use of these drugs may result in damage to normally healthy organs and tissues, and compromise the long term health of the patient.

Although more selective chemotherapeutic treatments have been developed based on knowledge of how cancer cells develop, for example, the anti-estrogen compound tamoxifen, the effectiveness of all chemotherapeutic treatments are subject to development of resistance to the drugs. In particular, the increased expression of cell membrane bound transporters, such as MdrI, produces a multidrug resistance phenotype characterized by increased efflux of drugs from the cell. These types of adaptation by cancer cells severely limit the effectiveness of certain classes of chemotherapeutic agents. Consequently, identification of other chemotherapeutic agents is critical for establishing therapies effective for attacking the heterogeneous nature of proliferative disease and for overcoming any resistance that may develop over the course of therapy with other compounds. Moreover, use of combinations of chemotherapeutic agents with differing properties and cellular targets increases the effectiveness of chemotherapy and limits the generation of drug resistance.

3. SUMMARY

In one aspect, the present disclosure provides 4-pyrimidineamine compounds that exhibit antiproliferative activity against a variety of different cell types, including a variety of different types of tumor cells. The compounds are generally 4-pyrimidineamines that include a non-amino substituent at the 2-carbon of the pyrimidine ring, a secondary amino substitutent at the 4-carbon of the pyrimidine ring and an electronegative substituent at the 5-position of the pyrimidine ring. One of the groups on the secondary amino substituent located at the 4-position of the pyrimidine ring is a substituted aryl, such as a substituted phenyl. The other group is non-aromatic in character and is typically a lower alkyl, which can be optionally substituted. The substituent at the 2-position of the pyrimidine ring can be aromatic or non-aromatic in character. In some embodiments, the substituent at the 2-position is selected from halo (e.g., fluoro, chloro, bromo or iodo), hydroxy, an optionally substituted lower alkoxy, an optionally substituted aryloxy, an optionally substituted arylalkyloxy, an optionally substituted aryl, an optionally substituted arylalkyl, and optionally substituted heteroaryl, an optionally substituted heteroarylalkyl and an optionally substituted lower alkyl-, aryl- or arylalkyl-sulfonate (e.g., mesylate, benzylsulfonate, tosylate, triflate, etc.).

In an illustrative embodiment, the 4-pyrimdineamine compounds are compounds according to structural formula (I):

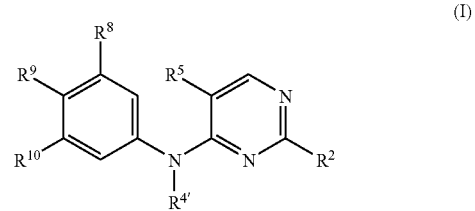

including salts, solvates, hydrates and oxides (e.g., N-oxides and S-oxides), wherein:
$R^2$ is selected from hydroxy, lower alkoxy optionally substituted with one or more of the same or different $R^d$ groups, C5-C14 aryloxy optionally substituted with one or more of the same or different $R^d$ groups, lower alkyl-, aryl- or arylalkyl-sulfonate optionally substituted with one or more of the same or different $R^d$ groups, halo, C5-C14 aryl optionally substituted with one or more of the same or different $R^d$ groups, C6-C20 arylalkyl optionally substituted with one or more of the same or different $R^d$ groups, 5-14-membered heteroaryl optionally substituted with one or more of the same or different $R^d$ groups and 6-20 membered heteroarylalkyl optionally substituted with one or more of the same or different $R^d$ groups;

$R^{4'}$ is a lower alkyl optionally substituted with one or more of the same or different $R^e$ groups;

$R^5$ is an electronegative group, such as, for example, an ester, a carboxyl, a halo (e.g., F, Cl, Br), a nitro, a cyano or a trifluoromethyl group;

R$^8$ is selected from hydrogen and halo;

R$^9$ is selected from hydroxy, lower alkoxy optionally substituted with one or more of the same or different R$^e$ groups, trifluoromethoxy and halo, or, alternatively, R$^9$ is taken together with R$^{10}$ to form a heteroalkylene bridge of the formula —O—(CR$^a$R$^a$)$_n$—O—, where n is 1, 2 or 3;

R$^{10}$ is selected from lower alkyl, lower alkoxy and halo or, alternatively, R$^{10}$ is taken together with R$^9$ to form a heteroalkylene bridge of the formula —O—(CR$^a$R$^a$)$_n$—O—, where n is 1, 2 or 3;

each R$^a$ is, independently of the others, selected from hydrogen and lower alkyl;

each R$^c$ is, independently of the other, selected from hydrogen and lower alkyl, or alternatively, two R$^c$ bonded to the same nitrogen atom may be taken together with that nitrogen atom to form a 5 to 7-membered heterocyclic ring that may optionally include from 1 to 4 of the same or different additional heteroatoms, for example selected from O, N and S, and which may optionally be substituted at one or more available carbon and/or nitrogen atoms with a lower alkyl group;

each R$^d$ is, independently of the others, selected from a water-solubilizing group, lower alkyl, halo, hydroxy, lower alkoxy, —C(O)R$^a$, and —(CH$_2$)$_m$NR$^c$R$^c$, where m is 0, 1, 2 or 3; and R$^e$ is selected from —NR$^c$R$^c$, —C(O)OR$^a$ and —C(O)NR$^c$R$^c$.

In another aspect, the present disclosure provides prodrugs of the 4-pyrimidineamine compounds. Such prodrugs may be active in their prodrug form, or may be inactive until converted under physiological or other conditions of use to an active drug form. In the prodrugs described herein, one or more functional groups of the 4-pyrimidineamine compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs described herein include special types of protecting groups, termed "progroups," masking one or more functional groups of the 4-pyrimidineamine compounds that cleave under the conditions of use to yield an active 4-pyrimidineamine drug compound. Functional groups within the 4-pyrimidineamine compounds that may be masked with progroups for inclusion in a promoiety include, but are not limited to, amines (primary and secondary), hydroxyls, sulfanyls (thiols), carboxyls, carbonyls, phenols, catechols, diols, alkynes, phosphates, etc. Myriad progroups suitable for masking such functional groups to yield promoieties that are cleavable under the desired conditions of use are known in the art. All of these progroups, alone or in combinations, may be included in the prodrugs described herein. Specific examples of promoieties that yield primary or secondary amine groups that can be included in the prodrugs described herein include, but are not limited to amides, carbamates, imines, ureas, phosphenyls, phosphoryls and sulfenyls. Specific examples of promoieties that cleave to yield hydroxyl groups that can be included in the prodrugs described herein include, but are not limited to, sulfonates, esters and carbonates. Specific examples of promoieties that yield carboxyl groups that can be included in the prodrugs described herein included, but are not limited to, esters (including silyl esters, oxamic acid esters and thioesters), amides and hydrazides.

Many of the 4-pyrimidineamine compounds described herein include substituents or moieties that can be converted into other substituents or moieties under in vivo conditions, such as via redox and/or hydrolysis reactions. As a specific example, in embodiments in which the R$^2$ group is a heteroaryl ring that includes a ring sulfur atom, the ring sulfur atom can be oxidized to a sulfoxide or a sulfone. As another specific example, compounds according to formula (I) in which R$^2$ is a chloro group (2-chloro-4-pyrimidineamine compounds) can undergo hydrolysis in vivo to yield the corresponding 2-hydroxy-4-pyrimidinemine compounds. Skilled artisans will recognize that these various redox and/or hydrolysis species can act as prodrugs of active compounds. As used herein, the expression "prodrug" is intended to include such redox and/or hydrolytic derivatives.

In another aspect, the present disclosure provides compositions comprising one or more of the 4-pyrimidineamine compounds and/or prodrugs described herein and an appropriate carrier, excipient or diluent. The exact nature of the carrier, excipient or diluent will depend upon the desired use for the composition, and may range from being suitable or acceptable for veterinary uses to being suitable or acceptable for human use.

The 4-pyrimidineamine compounds described herein are potent inhibitors of proliferation of abnormal cells, such as tumor cells, in in vitro assays. Thus, in still another aspect, the present disclosure provides methods of inhibiting proliferation of abnormal cells, in particular tumor cells. The method generally involves contacting an abnormal cell, such as a tumor cell, with an amount of a 4-pyrimidineamine compound or prodrug described herein, or an acceptable salt, hydrate, solvate, oxide and/or composition thereof, effective to inhibit its proliferation. The method may be practiced in in vitro contexts or in in vivo contexts as a therapeutic approach towards the treatment or prevention of proliferative disorders, such as tumorigenic cancers.

In another aspect, the present disclosure provides methods of treating proliferative disorders. The methods may be practiced in animals in veterinary contexts or in humans. The methods generally involve administering to an animal or human subject an amount of a 4-pyrimidineamine compound or prodrug described herein, or an acceptable salt, hydrate, solvate, oxide and/or composition thereof, effective to treat the disorder. Proliferative disorders that can be treated according to the methods described herein include, but are not limited to, tumorigenic cancers.

4. DETAILED DESCRIPTION OF THE PREFERRED EMBODIMENTS

4.1 Definitions

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta- 1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower akyl" refers to alkyl groups having from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. A "lower alkyldiyl" is an alkyldiyl group have from 1 to 6 carbon atoms. In preferred embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkylene groups include, but are not limited to, methano; ethylenes such as ethano, etheno, ethyno; propylenes such as propano, prop[1,2]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Cycloalkyl" by itself or as part of another substituent refer to a cyclic version of an "alkyl" group. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are phenyl and naphthyl.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Halogen" or "Halo" by themselves or as part of another substituent, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Heteroalkylene Bridge" by itself or as part of another substituent refers to an alkylene group in which one or more of the terminal and/or internal methylene groups is replaced with a heteroatom or heteroatomic group, such as for example, O, S or NH. Specific examples of the heteroalkylene bridges include, but are not limited to, —(CRR)$_x$—O—(CRR)$_y$—, —(CRR)$_x$—S—(CRR)$_y$—, —(CRR)$_x$—NH—(CRR)$_y$—, —O—(CRR)$_x$—O—, —S—(CRR)$_x$—O—, —S—(CRR)$_x$—S—, —NH—(CRR)$_x$—O—, —NH—(CRR)$_x$—S— and —NH—(CRR)$_x$—NH—, where each R is, independently of the others, selected from hydrogen and lower alkyl and x and y are each, independently of one another, an integer ranging from 1 to 6.

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

The above-defined groups may include prefixes and/or suffixes that are commonly used in the art to create additional well-recognized substituent groups. As examples, "alkyloxy" or "alkoxy" refers to a group of the formula —OR, "alkylamine" refers to a group of the formula —NHR and "dialkylamine" refers to a group of the formula —NRR, where each R is independently an alkyl. As another example, "haloalkoxy" or "haloalkyloxy" refers to a group of the formula —OR', where R' is a haloalkyl.

"Prodrug" refers to a derivative of an active 4-pyrimidineamine compound (drug) that may require a transformation under the conditions of use, such as within the body, to release the active 4-pyrimidineamine drug. Prodrugs are frequently, but not necessarily, pharmacologically inactive until converted into the active drug. Prodrugs are typically obtained by masking a functional group in an active 4-pyrimidineamine drug believed to be in part required for activity with a progroup (defined below) to form a promoiety which undergoes a transformation, such as cleavage, under the specified conditions of use to release the functional group, and hence the active 4-pyrimidineamine drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in active 4-pyrimidineamine compounds to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active 4-pyrimidineamine drug to form a promoiety, converts the drug into a prodrug. Progroups are typically attached to the functional group of the drug via bonds that are cleavable under specified conditions of use. Thus, a progroup is that portion of a promoiety that cleaves to reveal the functional group under the specified conditions of use. As a specific example, an amide promoiety of the formula —NH—C(O)CH$_3$ comprises the progroup —C(O)CH$_3$, which cleaves to reveal the drug functional group —NH$_2$. As anoher specific example, an ester promoiety —C(O)OCH$_3$ comprises the progroup —OCH$_3$, which cleaves to reveal the drug functional group —C(O)OH.

"Proliferative disorder" refers to a disease or disorder characterized by aberrant cell proliferation, for example where cells divide more than their counterpart normal cells. The aberrant proliferation may be caused by any mechanism of action or combination of mechanisms of action. For example, the cell cycle of one or more cells may be affected such that cell(s) divide more frequently than their counterpart normal cells, or alternatively, one or more cells may bypass inhibitory signals which would normally limit their number of divisions. Proliferative diseases include, but are not limited to, slow or fast growing tumors and cancers.

"Antiproliferative compound" refers to a compound that inhibits the proliferation of a cell as compared to an untreated control cell of a similar type. The inhibition can be brought about by any mechanism or combination of mechanisms, and may operate to inhibit proliferation cytostatically or cytotoxically. As a specific example, inhibition as used herein includes, but is not limited to, arrest of cell division, a reduction in the rate of cell division, proliferation and/or growth of a cell and/or induction of cell death.

"Pharmaceutically effective amount" or "therapeutically effective amount" refers to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or to decrease the growth rate of the tumor.

4.2 Antiproliferative 4-Pyrimidineamine Compounds

In some embodiments, the antiproliferative compounds are 4-pyrimidineamine compounds according to structural formula (I):

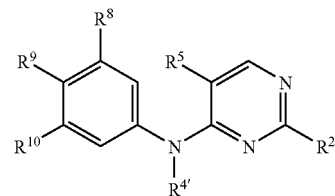

including prodrugs, salts, hydrates, solvates and oxides (e.g., N-oxides and S-oxides) thereof, wherein:
- $R^2$ is selected from hydroxy, lower alkoxy optionally substituted with one or more of the same or different $R^d$ groups, C5-C14 aryloxy optionally substituted with one or more of the same or different $R^d$ groups, lower alkyl-, aryl- or arylalkyl-sulfonate optionally substituted with one or more of the same or different $R^d$ groups, halo, C5-C14 aryl optionally substituted with one or more of the same or different $R^d$ groups, C6-C20 arylalkyl optionally substituted with one or more of the same or different $R^d$ groups, 5-14-membered heteroaryl optionally substituted with one or more of the same or different $R^d$ groups and 6-20 membered heteroarylalkyl optionally substituted with one or more of the same or different $R^d$ groups;
- $R^{4'}$ is a lower alkyl optionally substituted with one or more of the same or different $R^e$ groups;
- $R^5$ is an electronegative group, such as, for example, an ester, a carbonyl, a halo, fluoro, chloro, bromo, nitro, cyano or trifluoromethyl group;
- $R^8$ is selected from hydrogen and halo;
- $R^9$ is selected from hydroxy, lower alkoxy optionally substituted with one or more of the same or different $R^e$ groups, trifluoromethoxy and halo, or, alternatively, $R^9$ is taken together with $R^{10}$ to form a heteroalkylene bridge of the formula —O—(CR$^a$R$^a$)$_n$—O—, where n is 1, 2 or 3;
- $R^{10}$ is selected from lower alkyl, lower alkoxy and halo or, alternatively, $R^{10}$ is taken together with $R^9$ to form a heteroalkylene bridge of the formula —O—(CR$^a$R$^a$)$_n$—O—, where n is 1, 2 or 3;
- each $R^a$ is, independently of the others, selected from hydrogen and lower alkyl;
- each $R^c$ is, independently of the others, selected from hydrogen and lower alkyl, or, alternatively, two $R^c$ groups bonded to the same nitrogen atom may be taken together with that nitrogen atom to form a 5 to 7-membered heterocyclic ring which may optionally include from 1 to 4 additional heteroatoms, for example selected from O, S and N, and which may further optionally include a lower alkyl substituent at one or more available carbon and/or nitrogen atoms;
- each $R^d$ is, independently of the others, selected from a water-solubilizing group, lower alkyl, hydroxy, lower alkoxy, —C(O)R$^a$ and —(CH$_2$)$_m$NR$^c$R$^c$ where m is 0, 1, 2 or 3; and
- $R^e$ is selected from —NR$^c$R$^c$, —C(O)OR$^c$ and —C(O)NR$^c$R$^c$.

In some embodiments of the compounds described herein, when $R^8$, $R^9$ and $R^{10}$ are each hydrogen and/or $R^2$ is an optionally substituted 4-loweralkoxy-pyrid-6-yl, then $R^5$ is other than lower alkoxy or methoxy. In a specific embodiment, the compound is not N4-phenyl-2-(2-methyl-4-methoxy-pyrid-6-yl)-5-methoxy-4N-methyl-4-pyrimidineamine (compound 4.31 of DE 40 29 649 A1).

An important class of 4-pyrimidineamine compounds includes compounds according to structural formula (I), including the prodrugs, salts, hydrates, solvates and oxides thereof, in which $R^9$ and $R^{10}$ are taken together to form a heteroalkylene bridge of the formula —O—$(CH_2)_n$—O—, where n is 2, such that the compounds are 4-pyrimidineamines according to structural formula (II):

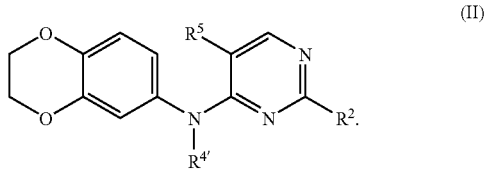

(II)

Another important class of 4-pyrimidineamine compounds includes compounds according to structural formulae (I) and/or (II), and the various prodrugs, salts, hydrates, solvates and oxides thereof, in which $R^5$ is other than cyano —$CH_2OH$, —$C(O)R^a$, —$C(O)OR^a$ and/or —$C(O)NR^cR^c$, where $R^a$ and $R^c$ are as previously defined for structural formula (I). In a specific embodiment, $R^5$ is selected from halo, trifluoromethyl, cyano and/or nitro. In another specific embodiment, $R^5$ is a halo group, preferably fluoro.

Still another important class of 4-pyrimidineamine compounds includes compounds according to structural formulae (I) and/or (II), and the various prodrugs, salts, hydrates, solvates and oxides thereof, in which $R^{4'}$ is an unsubstituted lower alkyl. In a specific embodiment, $R^{4'}$ is an unsubstituted C1-C3 n-alkanyl.

Still another important class of 4-pyrimidineamine compounds includes compound according to structural formulae (I) and/or (II), and the various prodrugs, salts, hydrates, solvates and oxides thereof, as well as any of the specific embodiments described herein, in which $R^2$ is halo group. In a specific embodiment, $R^2$ is chloro.

Skilled artisans will appreciate that compounds in which $R^2$ is a halo group, such as a chloro group, might undergo hydrolysis in vivo to yield the corresponding hydroxy compound, i.e., a compound according to structural formula (I) and/or (II) in which $R^2$ is hydroxyl. Thus, yet another important class of 4-pyrimidineamine compounds includes compounds according to structural formulae (I) and/or (II), and the various prodrugs, salts, hydrates, solvates and oxides thereof, as well as any of the specific embodiments described herein, in which $R^2$ is a hydroxyl group.

In other embodiments of the 4-pyrimidineamine compounds, such as the compounds of structural formulae (I) and (II), and the various prodrugs, salts, hydrates, solvates and oxides thereof, as well as any of the specific embodiments described herein, $R^2$ is an optionally substituted aryl, arylalkyl, heteroaryl or heteroarylalkyl group. Although the aryl or heteroaryl group (or aryl or heteroaryl moieties of the arylalkyl and heteroarylalkyl groups, respectively) may vary in the number of ring atoms, an aryl group will typically contain from 6 to 14 ring atoms and a heteroaryl group will typically contain from 5 to 15 ring atoms. Heteroaryl groups may include any number and any type of heteroatoms or heteroatomic groups in the ring. In some embodiments, the heteroatoms or heteroatomic groups are selected from O, S, H, NH and $NR^f$, where $R^f$ is lower alkyl, although other heteroatoms or heteroatomic groups may be used. Specific examples of suitable aryl and heteroaryl rings that may comprise substitutent $R^2$ in the 4-pyrimidineamine compounds described herein are provided above in connection with the definitions of aryl and heteroaryl, respectively.

In a specific embodiment, $R^2$ comprises an optionally unsubstituted phenyl group. In another specific embodiment, $R^2$ comprises an optionally substituted 5- or 6-membered heteroaryl group that includes a single heteroatom or heteroatomic group. In another compound, $R^2$ comprises a heteroaryl group illustrated in TABLE 1, infra. In still another specific embodiment, $R^2$ comprises an optionally substituted 5- or 6-membered heteroaryl group selected from furanyl (2-, 3-, 4- or 5-), thienyl (2-, 3-, 4- or 5-), pyrroly (2-, 3-. 4- or 5-) and pyridyl (2-, 3-, 4-, 5- or 6-).

The aryl or heteroaryl group may be optionally substituted with one or more of the same or different $R^d$ groups. These substitutent groups may be attached to any available ring carbon or atom or hetero atom. In some embodiments, the $R^2$ aryl or heteroaryl is substituted with a water-solubilizing group. As used herein, a "water-solubilizing" group is a group that has hydrophilic character sufficient to improve or increase the water-solubility of the compound in which it is included, as compared to an analog compound that does not include the group. The hydrophilic character can be achieved by any means, such as by the inclusion of functional groups that ionize under the conditions of use to form charged moieties (e.g., carboxylic acids, sulfonic acids and salts, phosphoric acids and salts, amines, etc.); groups that include permanent charges (e.g., quaternary ammonium groups); and/or heteroatoms or heteroatomic groups, for example, O, S, N, NH, N—$(CH_2)_y$—$R^a$, N—$(CH_2)_y$—$C(O)R^a$, N—$(CH_2)_y$—$C(O)OR^a$, N—$(CH_2)_y$—$S(O)_2R^a$, N—$(CH_2)_y$—$S(O)_2OR^a$, N—$(CH_2)_y$—$C(O)NR^aR^a$, etc., where $R^a$ is as previously defined for structural formula (I) and y is an integer ranging from 0 to 6. In some embodiments, the water-solubilizing group is a cycloheteroalkyl that optionally includes from 1 to 5 substituents, which may themselves be water-solubilizing groups. In a specific embodiment, the water-solubilizing group is of the forumula

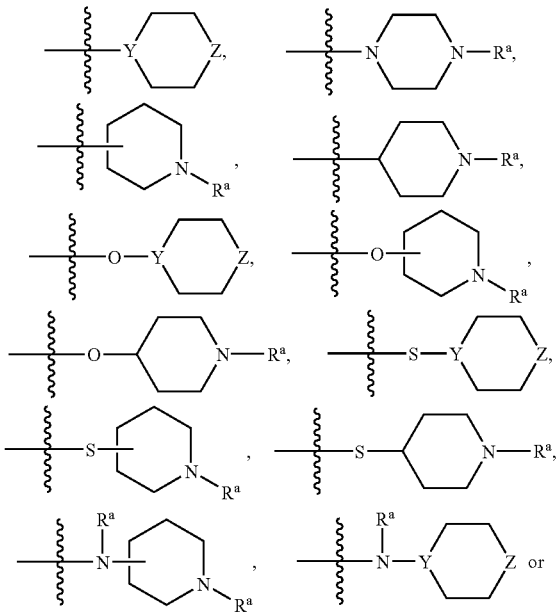

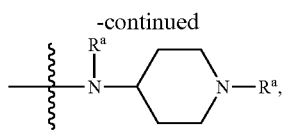

where Y is selected from CH and N and Z is selected from CH$_2$, O, S, N, NH, N—(CH$_2$)$_y$—R$^a$, N—(CH$_2$)$_y$—C(O)R$^a$, N—(CH$_2$)$_y$C(O)OR$^a$, N—(CH$_2$)$_y$—S(O)$_2$R$^a$, N—(CH$_2$)$_y$—S(O)$_2$OR$^a$ and N—(CH$_2$)$_y$—C(O)NR$^c$R$^c$, where R$^a$, R$^c$ and y are as previously defined, with the proviso that Y and Z are not both simultaneously CH and CH$_2$, respectively. In another specific embodiment, the water-solubilizing group is selected from morpholino, piperidinyl, lower N-alkyl piperidinyl, N-methyl piperidinyl, piperazinyl, lower N-alkylpiperazinyl, N-methylpiperazinyl, N-ethyl piperidinyl, N-ethyl piperazinyl, pyrrolidinyl, lower N-alkyl pyrrolidinyl, N-methylpyrrolidinyl, diazepinyl, N-ethyl pyrrolidinyl, lower N-alkyl azepinyl, N-methyl azepinyl, N-ethyl azepinyl, homopiperazinyl, N-methyl homopiperazinyl, N-ethyl homopiperazinyl, imidazoyl, and the like.

In some embodiments, R$^2$ is an optionally substituted phenyl. Specific examples of optionally substituted phenyls include phenyls that are optionally mono-, di- or tri-substituted with the same or different R$^d$ groups. When the phenyl is mono-substituted, the R$^d$ substituent may be positioned at either the ortho, meta or para position. When the phenyl is di-substituted or tri-substituted, the R$^d$ substituents may be positioned at any combination of positions. For example, the R$^d$ substituents may be positioned at the 2,3-, 2,4-, 2,5-, 2,6-, 3,4-, 3,5-, 2,3,4-, 2,3,5-, 2,3,6-, 2,4,5-, 2,4,6-, 2,5,6- or 3,4,5- positions of the phenyl ring. In some embodiments in which R$^2$ is a disubstituted phenyl, the substituents are positioned 3,4. In some embodiments in which R$^2$ is a trisubstituted phenyl, the substituents are positioned 2,3,4. In a specific embodiment, R$^d$ substituents useful for substituting such mono-, di-and trisubstituted phenyls are selected from —OR$^a$, —NR$^a$R$^a$ and (C1-C6) alkyl, where R$^a$ is as previously defined for structural formula (I). In a specific embodiment, R$^d$ substituents useful for substituting mono-, di-and trisubstituted phenyls are selected from —OH, —OMe and —NH$_2$. Specific examples of mono-substituted phenyl rings, di-substituted phenyl rings and tri-substituted phenyl rings are provided in TABLE 1, infra.

In some embodiments, the substituents at the 3- and 4-positions are taken together to form a heteroalkylene bridge of the formula —O—(CR$^a$R$^a$)$_m$—O—, where m is an integer ranging from 1 to 3 and each R$^a$ is, independently of the other, as previously defined for structural formula (I). In some embodiments, each R$^a$ is hydrogen. In a specific embodiment, R$^2$ is selected from

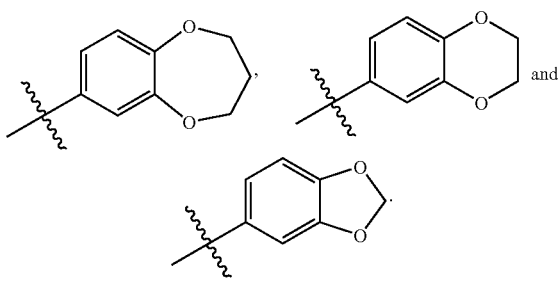

In other embodiments, R$^2$ is a heteroaryl optionally substituted with one or more of the same or different R$^d$ groups. Exemplary heteroaryl groups are illustrated in TABLE 1, infra. Suitable exemplary R$^d$ substituents include those described above in connection with the phenyl group.

Those of skill in the art will appreciate that the 4-pyrimidineamine compounds described herein may include functional groups that can be masked with progroups to create prodrugs. Such prodrugs are usually, but need not be, pharmacologically inactive until converted into their active drug form. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 4-pyrimidineamine compounds that include ester moieties may be considered prodrugs of their corresponding carboxylic acids, regardless of whether the ester form is pharmacologically active.

In the prodrugs described herein, any available functional moiety may be masked with a progroup to yield a prodrug. Functional groups within the 4-pyrimidineamine compounds that may be masked with progroups for inclusion in a promoiety include, but are not limited to, amines (primary and secondary), hydroxyls, carboxyls, etc. Myriad progroups suitable for masking such functional groups to yield promoieties that are cleavable under the desired conditions of use are known in the art. All of these progroups, alone or in combinations, may be included in the prodrugs described herein.

Many of the 4-pyrimidineamine compounds described herein include substituents or moieties that can be converted into other substituents or moieties under in vivo conditions, such as via redox and/or hydrolysis reactions. As a specific example, in embodiments in which the R$^2$ group is a heteroaryl ring that includes a ring sulfur atom, the ring sulfur atom can be oxidized to a sulfoxide or a sulfone. As another specific example, compounds according to formula (I) in which R$^2$ is a chloro group (2-chloro-4-pyrimidineamine compounds) can undergo hydrolysis in vivo to yield the corresponding 2-hydroxy-4-pyrimidinemine compounds. Skilled artisans will recognize that these various redox and/or hydrolysis species can act as prodrugs of active compounds. As used herein, the expression "prodrug" is intended to include such redox and/or hydrolytic derivatives.

Those of skill in the art will appreciate that many of the compounds and prodrugs described herein, as well as the various compound species specifically described and/or illustrated herein, may exhibit the phenomena of tautomerism, conformational isomerism, geometric isomerism and/or optical isomerism. For example, the compounds and prodrugs described herein may include one or more chiral centers and/or double bonds and, as a consequence, may exist as stereoisomers, such as double-bond isomers (i.e., geometric isomers), enantiomers and diasteromers and mixtures thereof, such as racemic mixtures. As another example, the compounds and prodrugs described herein may exist in several tautomeric forms, including enol forms, keto forms and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms. In cases of limited rotation around the 4-pyrimidineamine core structure atropisomers are also possible and are also specifically included in the compounds described herein. "Atropisomers" are stereoisomers resulting from hindered rotation about single bonds where the barrier to rotation is high enough to allow for the isolation of the conformers (see, e.g., Eliel, E. L. and Wilen, S. H., *Stereochemistry of Organic Compounds*, Wiley & Sons, New York, 1994, Chapter 14, including pages 1150-1153 and the short definition on page 1193). Atropisomerism is significant because it introduces an element of chirality in the absence of stereogenic atoms.

Moreover, skilled artisans will appreciate that when lists of alternative substituents include members which, owing to valency requirements or other reasons, cannot be used to substitute a particular group, the list is intended to be read in context to include only those members of the list that are suitable for substituting the particular group. For example, skilled artisans will appreciate that certain substituents that can be used to substitute an alkyl group, such as an oxo (=O) group, owing to valency requirements, cannot be used to substitute a phenyl group. It is to be understood that only possible combinations of substitutions and substituent-group pairs are intended.

The compounds and/or prodrugs described herein may be identified by either their chemical structures or their chemical names. When the chemical structure and the chemical name of a specific compound conflict, the chemical structure is intended to be determinative of the identity of the compound.

Depending upon the nature of the various substituents, the 4-pyrimidineamine compounds and prodrugs described herein may be in the form of salts. Such salts include salts suitable for pharmaceutical uses ("pharmaceutically-acceptable salts"), salts suitable for veterinary uses, etc. Such salts may be derived from acids or bases, as is well-known in the art.

In some embodiments, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, 2,4,6-trimethylbenzenesulfonic acid, etc.), 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The 4-pyrimidineamine compounds and/or prodrugs described herein, as well as the salts thereof, may also be in the form of hydrates, solvates and oxides (e.g., N-oxides, S-oxides, etc), as are well-known in the art.

4.3 Methods of Synthesis

The 4-pyrimidineamine compounds and prodrugs described herein may be synthesized via a variety of different synthetic routes using commercially available starting materials and/or starting materials prepared by conventional synthetic methods. Suitable exemplary methods that may be routinely used and/or adapted to synthesize 4-pyrimidineamine compounds and prodrugs described herein in which $R^2$ is a halo group, such as a chloro group, are found in U.S. Pat. No. 5,958,935 and copending commonly owned U.S. application Ser. No. 10/355,543, filed Jan. 31, 2003, the disclosures of which are incorporated herein by reference. Suitable exemplary methods that may be routinely used and/or adapted to synthesize 4-pyrimidineamine compounds and prodrugs described herein in which $R^2$ is an optionally substituted aryl, arylalkyl, heteroaryl or heteroarylalkyl group, are found in LoAse et al., 1999, Synlett. 1:45-48, the disclosure of which is incorporated herein by reference. All of the compounds described herein (including prodrugs) may be prepared by routine adaptation of these various methods.

An exemplary synthetic route that can be used to synthesize 4-pyrimidineamine compounds in which $R^2$ is a halo group is illustrated below in Scheme (I). This method may be routinely adapted to synthesize other 4-pyrimidineamine compounds and prodrugs described herein.

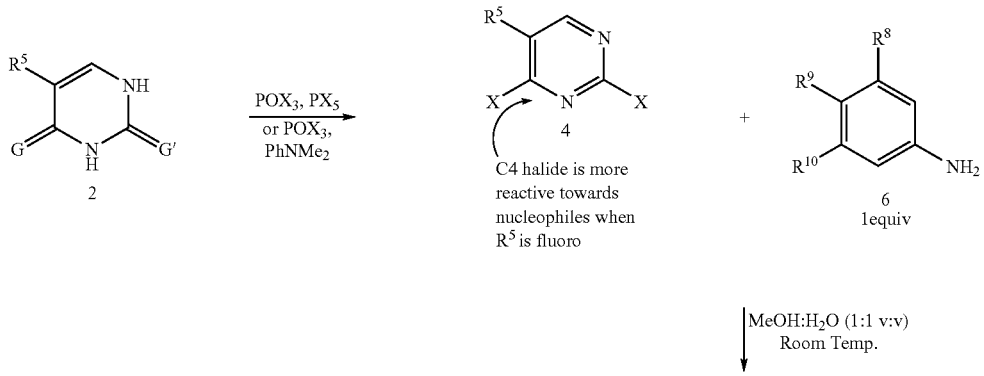

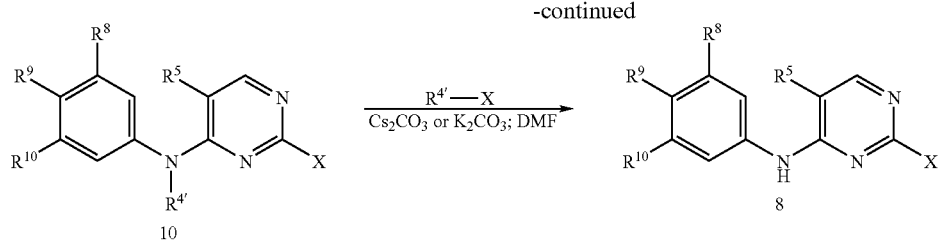

In Scheme (I), $R^{4'}$ and $R^5$ are as previously defined for structural formula (I), X is halo and G and G' are each, independently of one another, selected from O and S. According to Scheme (I), uracil or thiouracil 2 is dihalogenated at the 2- and 4-positions using standard chlorinating agent $POX_3$ (or other standard halogenating agent) in combination with $PX_5$ or $PhNMe_2$ under standard conditions to yield 2,4-bishalopyrimidine 4. When $R^5$ is a halo (e.g., fluoro, bromo, etc.) or cyano, due to the electron-withdrawing inductive effect of $R^5$ in 2,4-bishalopyrimidine 4, the halide at the C4 position is more reactive towards nucleophiles than the halide at the C2 position. This differential reactivity can be exploited to synthesize 2-halo-4-pyrimidineamines 8 by reacting 2,4-bishalopyrimidine 4 with one equivalent of aniline 6. While the C4 halide in 2,4-bishalopyrimidine 4 exhibits selective reactivity when $R^5$ is halo or cyano, as will be recognized by skilled artisans, the identity of the $R^5$ substituent may alter this selectivity. For example, when $R^5$ is trifluoromethyl, a 50:50 mixture of 4N-substituted-2-halo-pyrimidineamine 8 and the corresponding 2N-substituted-4-halo-pyrimidineamine (not illustrated) is obtained owing to the steric hindrance of the trifluoromethyl group. Regardless of the identity of the $R_5$ substituent, the regioselectivity of the reaction can be controlled by adjusting the solvent and other synthetic conditions (such as temperature), as is well-known in the art. Alternatively, the desired regio isomer 8 can be isolated using standard techniques.

The reaction of 2,4-bishalopyrimidine 4 with aniline 6 (typically 1 or more equiv) in 1:1 (v:v) methanol:$H_2O$ at room temperature yields the desired 2-halo-4-pyrimidineamine 8 as a precipitate. If the aniline has poor solubility, the reaction can be carried out in neat methanol at 60-70° C. Excess aniline 6 can be solubilized by acidification with 2N HCl (to pH 2) without affecting the precipitated 2-halo-4-pyrimidineamine 8. If excess 2,4-bishalopyrimidine 4 (or unreacted 2,4-bishalopyrimidine 4) is observed, it can be readily removed under vacuum, as it sublimes at approx. 37° C. (when $R^5$ is fluoro and X is Cl). The precipitated 2-halo-4-pyrimidineamine 8 can be isolated in very good yield and purity by diluting the reaction mixture with water, acidifying the diluate with 2N HCl (to pH 2), collecting the 2-halo-4-pyrimidineamine 8 precipitate by suction filtration and drying the precipitate under vacuum. Although the reaction Scheme (I) is illustrated with 1 equiv of aniline 6, either it, or 2,4-bishalopyrimidine 4 can be added in excess. For example, the reaction can be carried out with 1.5 equiv of 2,4-bishalopyrimidine 4 and 1 equiv aniline 6, or vice versa.

2-Halo-4-pyrimidineamines in which $R^{4'}$ is other than hydrogen can be prepared by reacting 2-halo-4-pyrimidineamine 8 with an alkyling reagent under standard conditions, as is well-known in the art. In the example illustrated in Scheme (I), 2-halo-4-pyrimidineamine 8 is reacted with halide $R^{4'}$—X, where X is a halo group, for example Cl or Br. The resultant compound 10 can be isolated via standard techniques.

The uracil or thiouracil 2 starting materials may be purchased from commercial sources or prepared using standard techniques of organic chemistry. Commercially available uracils and thiouracils that can be used as starting materials in Scheme (I) include, by way of example and not limitation, uracil (Aldrich #13,078-8; CAS Registry 66-22-8); 2-thiouracil (Aldrich #11,558-4; CAS Registry 141-90-2); 2,4-dithiouracil (Aldrich #15,846-1; CAS Registry 2001-93-6); 5-bromouracil (Aldrich #85,247-3; CAS Registry 51-20-7; 5-fluorouracil (Aldrich #85,847-1; CAS Registry 51-21-8); 5-iodouracil (Aldrich #85,785-8; CAS Registry 696-07-1); 5-nitrouracil (Aldrich #85,276-7; CAS Registry 611-08-5); 5-(trifluoromethyl)-uracil (Aldrich #22,327-1; CAS Registry 54-20-6). Additional 5-substituted uracils and/or thiouracils are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

Aniline 6 may be purchased from commercial sources or, alternatively, may be synthesized utilizing standard techniques. For example, suitable anilines may be synthesized from nitro precursors using standard chemistry. Specific examples for synthesizing suitable anilines can be found, for example, in copending commonly owned U.S. application Ser. No. 10/355,543, filed Jan. 31, 2003, the disclosure of which are incorporated herein by reference. See also, Vogel, 1989, *Practical Organic Chemistry*, Addison Wesley Longman, Ltd. and John Wiley & Sons, Inc.

Skilled artisans will recognize that in some instances, aniline 6 may include functional groups that require protection during synthesis. The exact identity of any protecting group(s) used will depend upon the identity of the functional group being protected, and will be apparent to these of skill in the art. Guidance for selecting appropriate protecting groups, as well as synthetic strategies for their attachment and removal, may be found, for example, in Greene & Wuts, *Protective Groups in Organic Synthesis,* 3d Edition, John Wiley & Sons, Inc., New York (1999) and the references cited therein (hereinafter "Greene & Wuts"), the disclosures of which are incorporated herein by reference.

4-Pyrimidineamine compounds in which $R^2$ is other than a halo can be synthesized as illustrated in Scheme (II), below.

Scheme (II)

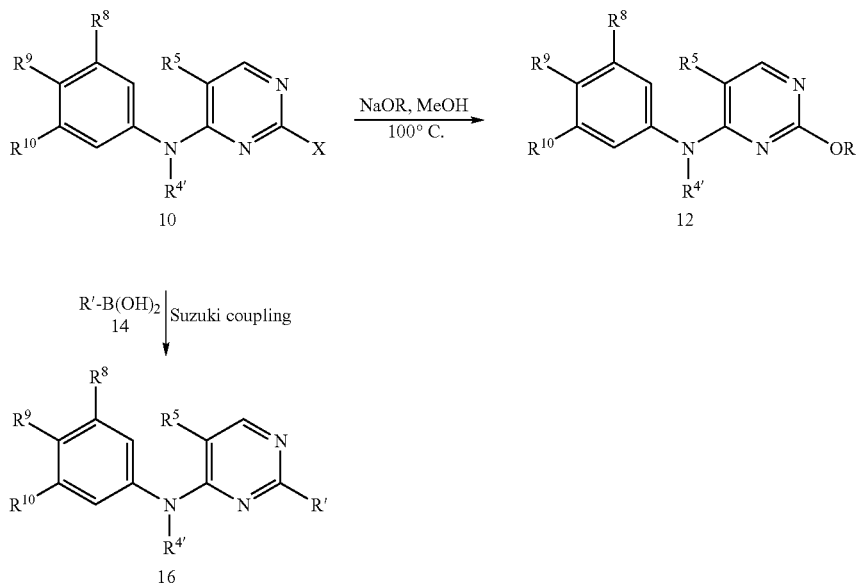

In Scheme (II), $R^{4'}$, $R^5$ and X are as previously defined for Scheme (I), $R^8$, $R^9$ and $R^{10}$ are as previously defined for structural formula (I), R is hydrogen or alkyl and R' is an optionally substituted aryl or heteroaryl. According to Scheme (II), 2-alkoxy-4-pyrimidine compounds 12 can be prepared by reacting 2-halo-4-pyrimidine 8 or 10 (see Scheme I, supra) with an appropriate sodium alkoxide in methanol at 100° C. 4-Pyrimidineamines 16 which are substituted at the 2-position with an optionally substituted aryl or heteraryl can also be prepared from 2-halo-4-pyrimidine 8 or 10 by reacting it with aryl- or heteroaryl-boronic acid 14 under Suzuki coupling conditions (see, e.g., Miyaura et al., 1979, Tetrahedron Lett. 1979:3437; Miyaura & Suzuki, 1979, Chem. Commun. 1979:866; Marck et al., 1993, Tetrahedron Lett. 34:3599; Wallow et al., 1994, J. Org. Chem. 59:5034; Suzuki, 1991, Pure Appl. Chem. 63:419-422; Martin & Yang, 1993, Acta Chem. Scand. 47:221-230). Additional synthetic routes are described in LoAse et al., 1999, Synlett 1:45-48 and the references cited therein, which are incorporated herein by reference. Although exemplary Scheme II illustrates Suzuki coupling, skilled artisans will appreciate that other coupling reactions, such as, for example, Stille coupling (see, e.g., Kosugi et al., 1977, Chem. Letters 1977:301; Milstein & Stille, 1978, J. Am. Chem. Soc. 100:3636; Stille, 1986, Agnew. Chem. Intl. Ed. 25:508-524; Pereyre et al., *Tin In Organic Synthesis*, Butterworths, Boston, 1987, pp. 185-207; Mitchell, 1992, Synthesis 1992:803-815) or Sonogashira coupling (see, e.g., Sonogashira et al., 1975, Tetrahedron Lett. 1975:4467; Rossi et al., 1995, Org. Prep. Proceed. Int. 27:129-160; Miller & Johnson, 1977, J. Org. Chem. 62:1582-1583) could also be used.

As for aniline 6, reagents used in Scheme (II) may include functional groups that require protection during synthesis. Guidance for selecting appropriate protecting groups, as well as synthetic strategies for their attachment and removal, may be found, for example, in Greene & Wuts, supra.

Prodrugs as described herein may be prepared by routine modification of the above-described method. Alternatively, such prodrugs may be prepared by reacting a suitably protected 4-pyrimidineamine of structural formula (I) with a suitable progroup. Conditions for carrying out such reactions and for deprotecting the product to yield a prodrugs as described herein are well-known. Myriad references teaching methods useful for synthesizing pyrimidines generally, as well as starting materials described in Scheme (I), are known in the art. For specific guidance, the reader is referred to Brown, D. J., "The Pyrimidines", in *The Chemistry of Heterocyclic Compounds*, Volume 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume 16, Supplement II* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume 16, Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds*, Volume 52 (Weissberger, A. and Taylor, E. C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidine synthesis pp. 313-316; amino pyrimidine synthesis pp. 315); Joule, J. A., Mills, K. and Smith, G. F., Heterocyclic Chemistry, 3$^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, 4$^{th}$ Edition, 2000, Blackwell Science, Ltd, Oxford, UK, pp. 1-589; *Comprehensive Organic Synthesis*, Volumes 1-9 (Trost, B. M. and Fleming, I., Ed.), 1991, Pergamon Press, Oxford, UK; *Comprehensive Heterocyclic Chemistry*, A. R. Katritzky and C. W. Reese, Ed. 1985, Vol. 1-8, Permagon Press, Oxford, UK; and *Comprehensive Heterocyclic Chemistry II*, A. R. Katritzky, Ed. 1996, Vol. 1-11, Permagon Press, Oxford, UK.

4.4 Activity of the Antiproliferative Compounds

Active compounds described herein typically inhibit proliferation of desired cells, such as tumor cells, with an $IC_{50}$ in the range of about 1 mM or less, as measured in a standard in vitro cellular proliferation assay. Of course, skilled artisans will appreciate that compounds which exhibit lower $IC_{50}$s, for example on the order of 100 μM, 10 μM, 1 μM, 100 nM, 10 nM, 1 nM, or even lower, may be particularly useful in therapeutic applications. The antiproliferative activity may be cytostatic or it may be cytotoxic. In instances where antiproliferative activity specific to a particular cell type is desired, the compound may be screened for activity with the desired cell type and counter-screened for a lack of activity against other cell types. The desired cell types and the desired degree of "inactivity" in such counter screens, or the desired ratio of activity vs. inactivity, may vary for different situations, and may be selected by the user.

4.5 Uses of the Antiproliferative Compounds

The antiproliferative 4-pyrimidineamine compounds, including the various salts, prodrugs, hydrates, solvates and oxide forms thereof (e.g. N-oxides and/or S-oxides), may be used to inhibit cell proliferation in a variety of contexts. In some embodiments, a cell or population of cells is contacted with an amount of such a compound effective to inhibit proliferation of the cell or cell population. The compound may act cytotoxically to kill the cell, or cytostatically to inhibit proliferation without killing the cell.

In a specific embodiment, the methods may be practiced as a therapeutic approach towards the treatment of proliferative disorders. Thus, in a specific embodiment, the 4-pyrimidineamine compounds (and the various forms described herein) may be used to treat proliferative disorders in animal subjects, including humans. The method generally comprises administering to the subject an amount of a compound described herein, or a salt, prodrug, hydrate, solvate or N-oxide thereof, effective to treat the disorder. In one embodiment, the subject is a mammal, including, but not limited to, bovine, horse, feline, canine, rodent, or primate. In another embodiment, the subject is a human.

A variety of cellular proliferative disorders may be treated with the compounds of the present invention. In some embodiments, the compounds are used to treat various cancers in afflicted subjects. Cancers are traditionally classified based on the tissue and cell type from which the cancer cells originate. Carcinomas are considered cancers arising from epithelial cells, while sarcomas are considered cancers arising from connective tissue or muscle. Other cancer types include leukemias, which arise from hematopoietic cells, and cancers of nervous system cells, which arise from neural tissue. For non-invasive tumors, adenomas are considered benign epithelial tumors with glandular organization, while chondomas are benign tumors arising from cartilage. In the methods described herein, the described compounds may be used to treat proliferative disorders encompassed by carcinomas, sarcomas, leukemias, neural cell tumors, and/or non-invasive tumors. In a specific embodiment, the compounds are used to treat solid tumors arising from various tissue types, including, but not limited to, tumors of the bone, breast, respiratory tract, brain, reproductive organs, digestive tract, urinary tract, eye, liver, skin, head, neck, thyroid, parathyroid, pancreas, kidney, and metastatic forms thereof.

Exemplary proliferative disorders that can be treated according to the methods described herein include, but are not limited to, the following: a) proliferative disorders of the breast include, but are not limited to, invasive ductal carcinoma, invasive lobular carcinoma, ductal carcinoma, lobular carcinoma in situ, and metastatic breast cancer; b) proliferative disorders of the skin include, but are not limited to, basal cell carcinoma, squamous cell carcinoma, malignant melanoma, and Karposi's sarcoma; c) proliferative disorders of the respiratory tract include, but are not limited to, small cell and non-small cell lung carcinoma, bronchial adema, pleuropulmonary blastoma, and malignant mesothelioma; d) proliferative disorders of the brain include, but are not limited to, brain stem and hyptothalamic glioma, cerebellar and cerebral astrocytoma, medullablastoma, ependymal tumors, oligodendroglial, meningiomas, and neuroectodermal and pineal tumors; e) proliferative disorders of the male reproductive organs include, but are not limited to, prostate cancer, testicular cancer, and penile cancer f) proliferative disorders of the female reproductive organs include, but are not limited to, uterine cancer (endometrial), cervical, ovarian, vaginal, vulval cancers, uterine sarcoma, ovarian germ cell tumor; g) proliferative disorders of the digestive tract include, but are not limited to, anal, colon, colorectal, esophageal, gallbladder, stomach (gastric), pancreatic cancer, pancreatic cancer-Islet cell, rectal, small-intestine, and salivary gland cancers; h) proliferative disorders of the liver include, but are not limited to, hepatocellular carcinoma, cholangiocarcinoma, mixed hepatocellular cholangiocarcinoma, and primary liver cancer; i) proliferative disorders of the eye include, but are not limited to, intraocular melanoma, retinoblastoma, and rhabdomyosarcoma; j) proliferative disorders of the head and cancers include, but are not limited to, laryngeal, hypopharyngeal, nasopharyngeal, oropharyngeal cancers, and lip and oral cancer, squamous neck cancer, metastatic paranasal sinus cancer; k) proliferative disorders of the lymphomas include, but are not limited to, various T cell and B cell lymphomas, non-Hodgkins lymphoma, cutaneous T cell lymphoma, Hodgkins disease, and lymphoma of the central nervous system; l) leukemias include, but are not limited to, acute myeloid leukemia, acute lymphoblastic leukemia, chronic lymphocytic leukemia, chronic myelogenous leukemia, and hair cell leukemia, m) proliferative disorders of the thyroid include thyroid cancer, thymoma, and malignant thymoma; n) sarcomas include, but are not limited to, sarcoma of the soft tissue, osteosarcoma, malignant fibrous histiocytoma, lymphosarcoma, and rhabdomyosarcoma.

It is to be understood that the descriptions of proliferative disorders is not limited to the conditions described above, but encompasses other disorders characterized by uncontrolled growth and malignancy. It is further understood that proliferative disorders include various metastatic forms of the tumor and cancer types described herein. The compounds of the present invention may be tested for effectiveness against the disorders as described herein, and a therapeutically effective regimen established. Effectiveness, as further described below, includes reduction or remission of the tumor, decreases in the rate of cell proliferation, or cytostatic or cytotoxic effect on cell growth.

4.6 Combination Therapies

The compounds and/or prodrugs described herein may be used alone, in combination with one another, or as an adjunct to, or in conjunction with, other established antiproliferative therapies. In some embodiments, the compounds and/or prodrugs may be used with traditional cancer therapies, such as ionization radiation in the form of γ-rays and x-rays, delivered externally or internally by implantation of radioactive compounds, and as a follow-up to surgical removal of tumors.

In some embodiments, the compounds and/or prodrugs described herein may be used with other chemotherapeutic agents useful for the disorder or condition being treated. These compounds may be administered simultaneously or sequentially, by the same routes of administration, or by different routes.

In some embodiments, the compounds and/or prodrugs described herein may be used with other anti-cancer (anti-neoplastic) or cytotoxic agents. Various classes of anti-cancer and anti-neoplastic compounds include, but are not limited to, alkylating agents, antimetabolites, vinca alkyloids, taxanes, antibiotics, enzymes, cytokines, platinum coordination complexes, substituted ureas, tyrosine kinase inhibitors, hormones and hormone antagonists. Exemplary alkylating agents include, by way of example and not limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil, cytosine arbinoside; purine analogs mecaptopurine, thioguanine, and azathioprine. Exemplary vinca alkyloids include, by way of example and not limitation, navelbine® (vinorelbine tartrate), vinblastine, vincristine, paclitaxel, and colchicine. Exemplary antibiotics include, by way of example and not limitation, actinomycin D, daunorubicin, and bleomycin. An exemplary enzyme effective as anti-neoplastic agents include L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesteron caproate, medroxyprogesterone; and anti-estrogen compound tamoxifen.

These and other useful anti-cancer compounds are described in *Merck Index*, 13th Ed. (O'Neil M. J. et al., ed) Merck Publishing Group (2001) and *Goodman and Gilmans The Pharmacological Basis of Therapeutics*, 10th Edition, Hardman, J. G. and Limbird, L. E. eds., pg. 1381-1287, McGraw Hill, (1996), both of which are incorporated by reference herein.

Additional anti-proliferative compounds useful in combination with the compounds of the present invention include, by way of example and not limitation, antibodies directed against growth factor receptors (e.g., anti-Her2); antibodies for activating T cells (e.g., anti-CTLA-4 antibodies); and cytokines such as interferon-α and interferon-γ, interleukin-2, and GM-CSF.

4.7 Formulations and Administration

When used to treat or prevent such proliferative diseases, the active compounds and/or prodrugs may be administered singly, as mixtures of one or more active compounds and/or prodrugs or in mixture or combination with other agents useful for treating such diseases and/or the symptoms associated with such diseases. The active compounds and/or prodrugs may also be administered in mixture or in combination with agents useful to treat other disorders or maladies, such as steroids, membrane stablizers, etc. The active compounds and/or prodrugs may be administered per se, or as pharmaceutical compositions, comprising an active compound and/or prodrug.

Pharmaceutical compositions comprising the active compounds and/or prodrugs described herein may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically (see, e.g., *Remingtons: The Science and Practice of Pharmacy*, 21st Ed., Lippincott, Williams & Wilkens, 2005).

The active compound and/or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions described herein may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate, lecithin). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

For prolonged delivery, the active compound(s) and/or prodrug(s) can be formulated as a depot preparation for administration by implantation or intramuscular injection. The active ingredient(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

4.8 Effective Dosages

The active compound(s) and/or prodrug(s) described herein, or compositions thereof, will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

The amount of compound administered will depend upon a variety of factors, including, for example, the particular indication being treated, the mode of administration, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in an in vitro assay, such as the in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pergamon Press, and the references cited therein. Effective dosages of prodrugs can estimated initially from $IC_{50}$ data for the active metabolized compound in conjunction with pharmacokinetic data to provide a circulating blood or serum concentration of the active (drug) compound that is at or above its $IC_{50}$.

Initial dosages may also be estimated from in vivo data, such as animal models. Animal models useful for testing the efficacy of compounds to treat or prevent the various proliferative diseases described above are well-known in the art. Dosage amounts will typically be in the range of from about 0.0001, 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) $LD_{50}/ED_{50}$ effect is the therapeutic index ($LD_{50}$ is the dose lethal to 50% of the population and $ED_{50}$ is the dose therapeutically effective in 50% of the population). Compounds(s) that exhibit high therapeutic indices are preferred.

4.9 Kits

The compounds and/or prodrugs described herein may be assembled in the form of kits. The kit provides the compound and reagents to prepare a composition for administration. The composition may be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In one embodiment, the therapeutic agents are other anti-cancer and anti-neoplastic compounds. These compounds may be provided in a separate form, or mixed with the compounds of the present invention.

The kits may include appropriate instructions for preparation and administration of the composition, side effects of the compositions, and any other relevant information. The instructions may be in any suitable format, including, but not limited to, printed matter, videotape, computer readable disk, or optical disc.

5. EXAMPLES 5.1 Compound Syntheses 5.1.1 Synthesis of 2-chloro-N-4-(3,4-ethylenedioxyphenyl)-5-fluoro-N-4-methyl-4-pyrimidineamine (Compound 1)

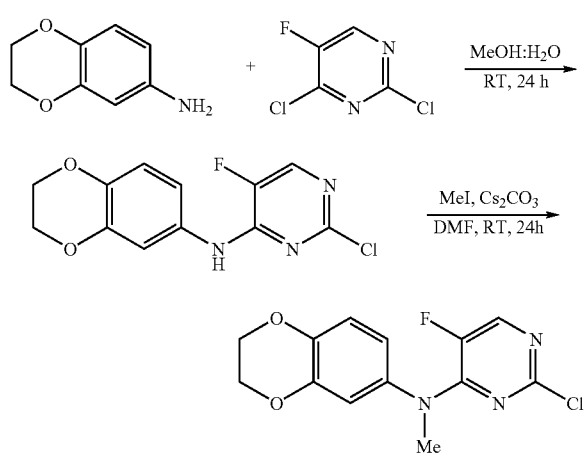

A reaction flask equipped with a magnetic stirring bar and a rubber septum (to prevent loss of 2,4-dichloro-5-fluoropyrimidine and $N_2$ inlet was charged with 3,4-ethylenedioxyaniline (34 g, 225 mmol), MeOH (100 mL), $H_2O$ (300 mL) and 2,4-dichloro-5-fluoropyrimidine (25 g, 150 mmol). The reaction mixture was stirred at room temperature for 1 h, diluted with $H_2O$ (1.5 liter), acidified with 2N HCl (200 mL) and sonicated. The solid obtained was filtered, washed with $H_2O$ and dried to obtain 33 g (78%) of the desired product, 2-chloro-N-4-(3,4-ethylenedioxyphenyl)-5-fluoro-4-pyrimidineamine. $^1$H NMR (CDCl$_3$): δ 8.02 (1H, d, J=3 Hz), 7.25 (d, 1H, J=1.2 Hz), 6.98 (dd, 1H, J=2.4 and 8.1 Hz), 6.85 (d, 1H, J=5.7 Hz), 4.27 (m, 4H); $^{19}$F NMR (CDCl$_3$): -44570; LCMS: ret. time: 26.70 min.; purity 100%; MS (m/e): 283 (MH$^+$).

A dry reaction flask equipped with a stirring bar and a nitrogen inlet was charged with 2-chloro-N-4-(3,4-ethylenedioxyphenyl)-5-fluoro-4-pyrimidineamine (0.282 g, 1 mmol), $Cs_2CO_3$ (0.650 g, 2 mmol) followed by N,N-dimethylformamide (5 mL). To this heterogeneous mixture was added methyl iodide (0.156 g, 1.1 mmol) at 0° C. and the resulting reaction was stirred at room temperature for 24 hours. The reaction was then quenched with water (50 mL), extracted with ethyl acetate (3×20 mL), the organic solution was dried over anhydrous sodium sulfate and solvent was evaporated under reduced pressure. The resulting residue was purified by column chromatography (silica gel, $CH_2Cl_2$ then 1% 2N $NH_3$/MeOH in $CH_2Cl_2$) to obtain 2-chloro-N-4-(3,4-ethylenedioxyphenyl)-5-fluoro-N-4-methyl-4-pyrimidineamine (Compound 1).

5.1.2 Synthesis of N4-(3,4-ethylenedioxyphenyl)-5-fluoro-2-(2-formylthien-3-yl)-N-4-methyl-4-pyrimidineamine (Compound 39) via Suzuki Coupling Reaction

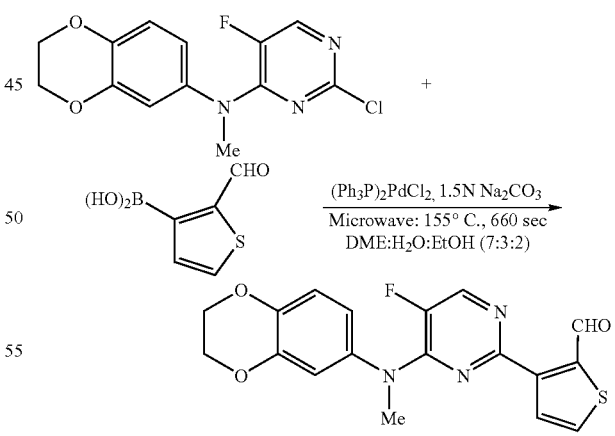

A mixture of 2-chloro-N-4-(3,4-ethylenedioxyphenyl)-5-fluoro-N-4-methyl-4-pyrimidineamine (50 mg, 0.17 mmol), (2-formylthien-3-yl)boronic acid (40 mg, 0.26 mmole), dichlorobis(triphenylphosphine)palladium(II) (25 mg, 0.035 mmol), and 1.5 N $Na_2CO_3$ (0.128 mL, 0.187 mmol) in 0.50 mL solvent (DME:$H_2O$:EtOH, 7:3:2; v/v/v) was added to a sealed microwave tube. The reaction mixture was heated in microwave at 155° C. for 660 seconds. After cooling to room temperature, the reaction mixture was filtered through Celite and the filter cake washed with methanol. Concentration in vacuo gave the crude product, which was purified by chromatography (silica gel, eluted with 1% ethyl acetate in hexanes ramped up to 20% ethyl acetate in hexanes). $^1$H NMR (CDCl$_3$): δ 10.74 (s, 1H), 8.01 (d, J=5.4 Hz, 1H), 7.77 (d, J=5.4 Hz, 1H), 7.55 (dd, J=1.2 and 5.4 Hz, 1H), 6.79 (d, J=8.7 Hz, 1H), 6.68 (d, J=2.1 Hz, 1H), 6.63 (dd, J=2.4 and 8.4 Hz, 1H), 4.21 (s, 4H), 3.43 (s, 3H); LCMS: purity: 91%; MS (m/e): 372 (MH$^+$).

5.1.3 Synthesis of Additional Compounds via Suzuki Coupling Reaction

The following additional compounds were synthesized analogously employing the above-described Suzuki coupling reaction and the appropriate boronic acid:

N4-(3,4-Ethylenedioxyphenyl)-5-fluoro-N-4-methyl-2-(phenyl)-4-pyrimidineamine (Compound 18): $^1$H NMR (DMSO-d$_6$): δ 8.35-8.28 (m, 2H), 8.26 (dd, J=0.9 and 5.4 Hz, 1H), 7.50-7.43 (m, 3H), 6.91-6.78 (m, 3H), 4.25 (s, 4H), 3.49 (s, 3H); LCMS: purity: 99%; MS (m/e): 338 (MH$^+$).

N4-(3,4-Ethylenedioxyphenyl)-5-fluoro-2-(3-hydroxyphenyl)-N-4-methyl-4-pyrimidineamine (Compound 19): $^1$H NMR (DMSO-d$_6$): δ 9.53 (s, 1H), 8.23 (d, J=6.0 Hz, 1H), 7.76-7.71 (m, 2H), 7.25 (t, J=8.1 Hz, 1H), 6.90-6.77 (m, 4H), 4.25 (s, 4H), 3.48 (s, 3H); LCMS: purity: 98%; MS (m/e): 354 (MH$^+$).

N4-(3,4-Ethylenedioxyphenyl)-2-(3,4-dimethoxyphenyl)-5-fluoro-N-4-methyl-4-pyrimidineamine (Compound 20): $^1$H NMR (DMSO-d$_6$): δ 8.21 (d, J=5.7 Hz, 1H), 7.88 (dd, J=1.8 and 8.1 Hz, 1H), 7.86-7.83 (m, 1H), 7.03 (d, J=8.7 Hz, 1H), 6.90-6.76 (m, 3H), 4.25 (s, 4H), 3.81 (s, 6H), 3.49 (s, 3H); LCMS: purity: 99%; MS (m/e): 398 (MH$^+$).

N4-(3,4-Ethylenedioxyphenyl)-5-fluoro-N-4-methyl-2-(3,4-methylenedioxyphenyl)-4-pyrimidineamine (Compound 21): $^1$H NMR (DMSO-d$_6$): δ 8.20 (d, J=5.7 Hz, 1H), 7.89 (dd, J=1.5 and 8.4 Hz, 1H), 7.74 (d, J=1.5 Hz, 1H), 6.99 (d, J=8.4 Hz, 1H), 6.90-6.76 (m, 3H), 6.08 (s, 2H), 4.25 (s, 4H), 3.46 (s, 3H); LCMS: purity: 98%; MS (m/e): 382 (MH$^+$).

N4-(3,4-Ethylenedioxyphenyl)-5-fluoro-2-(2-furyl)-N-4-methyl-4-pyrimidineamine (Compound 22): $^1$H NMR (DMSO-d$_6$): δ 8.17 (d, J=5.4 Hz, 1H), 7.86-7.83 (m, 1H), 7.16-7.14 (m, 1H), 6.90-6.75 (m, 3H), 6.65-6.61 (m, 1H), 4.25 (s, 4H), 3.43 (s, 3H); LCMS: purity: 99%; MS (m/e): 328 (MH$^+$).

2-(3-Aminophenyl)-N-4-(3,4-ethylenedioxyphenyl)-5-fluoro-N-4-methyl-4-pyrimidineamine (Compound 23): $^1$H NMR (DMSO-d$_6$): δ 8.20 (d, J=5.4 Hz, 1H), 7.59-7.56 (m, 1H), 7.47 (d, J=8.1 Hz, 1H), 7.09 (t, J=7.8 Hz, 1H), 6.89-6.76 (m, 3H), 6.67-6.62 (m, 1H), 5.18 (s, 2H), 4.25 (s, 4H), 3.48 (s, 3H); LCMS: purity: 98%; MS (m/e): 353 (MH$^+$).

N4-(3,4-Ethylenedioxyphenyl)-5-fluoro-N-4-methyl-2-(3-thienyl)-4-pyrimidineamine (Compound 25): $^1$H NMR (DMSO-d$_6$): δ 8.21-8.23 (m, 1H), 8.18 (d, J=5.7 Hz, 1H), 7.73-7.70 (m, 1H), 7.61-7.57 (m, 1H), 6.90-6376 (m, 3H), 4.25 (s, 4H), 3.46 (s, 3H); LCMS: purity: 99%; MS (m/e): 344 (MH$^+$).

N4-(3,4-Ethylenedioxyphenyl)-5-fluoro-2-(3-furyl)-N-4-methyl-4-pyrimidineamine (Compound 26): $^1$H NMR (DMSO-d$_6$): δ 8.29-8.27 (m, 1H), 8.14 (d, J=6.0 Hz, 1H), 7.74 (t, J=1.8 Hz, 1H), 6.93 (dd, J=0.6 and 1.5 Hz, 1H), 6.88-6.81 (m, 2H), 6.77 (dd, J=2.4 and 8.4 Hz, 1H), 4.24 (s, 4H), 3.43 (s, 3H); LCMS: purity: 99%; MS (m/e): 328 (MH$^+$).

N4-(3,4-Ethylenedioxyphenyl)-5-fluoro-N-4-methyl-2-(pyridin-3-yl)-4-pyrimidineamine (Compound 27): $^1$H NMR (DMSO-d$_6$): δ 9.42 (d, J=1.2 Hz, 1H), 8.65 (dd, J=1.8 and 5.1 Hz, 1H), 8.57 (dt, J=1.8 and 8.1 Hz, 1H), 8.30 (d, J=5.1 Hz, 1H), 7.51 (dd, J=4.8 and 7.5 Hz, 1H), 6.91 (d, J=2.4 Hz, 1H), 6.88-6.78 (m, 2H), 4.25 (s, 4H), 3.50 (s, 3H); LCMS: purity: 99%; MS (m/e): 339 (MH$^+$).

N4-(3,4-Ethylenedioxyphenyl)-5-fluoro-N-4-methyl-2-(pyridin-4-yl)-4-pyrimidineamine (Compound 28): $^1$H NMR (DMSO-d$_6$): δ 8.70 (d, J=6.3 Hz, 2H), 8.30 (d, J=5.4 Hz, 1H), 8.14 (d, J=6.3 Hz, 2H), 6.90-6.86 (m, 1H), 6.83-6.78 (m, 1H), 4.26 (s, 4H), 3.52 (s, 3H); LCMS: purity: 98%; MS (m/e): 339 (MH$^+$).

2-(3,5-Dimethylisoxazol-4-yl)-N-4-(3,4-ethylenedioxyphenyl)-5-fluoro-N-4-methyl-4-pyrimidineamine (Compound 29): $^1$H NMR (DMSO-d$_6$): δ 8.23 (d, J=6.0 Hz, 1H), 6.90-6.82 (m, 2H), 6.78 (dd, J=2.7 and 8.7 Hz, 1H), 4.24 (s, 4H), 3.42 (s, 3H), 2.70 (s, 3H), 2.46 (s, 3H); LCMS: purity: 98%; MS (m/e): 357 (MH$^+$).

N4-(3,4-Ethylenedioxyphenyl)-5-fluoro-N-4-methyl-2-(thiazol-2-yl)-4-pyrimidineamine (Compound 30): $^1$H NMR (DMSO-d$_6$): δ 8.27 (d, J=6.0 Hz, 1H), 7.99 (d, J=3.3 Hz, 1H), 7.89 (d, J=3.3 Hz, 1H), 6.93 (d, J=2.1 Hz, 1H), 6.88-6.80 (m, 2H), 4.25 (s, 4H), 3.46 (s, 3H); LCMS: purity: 99%; MS (m/e): 345 (MH$^+$).

N4-(3,4-Ethylenedioxyphenyl)-5-fluoro-N-4-methyl-2-(1H-pyrrol-2-yl)-4-pyrimidineamine (Compound 31): $^1$H NMR (DMSO-d$_6$): δ 11.36 (s, 1H), 8.07 (d, J=6.0 Hz, 1H), 6.90-6.81 (m, 3H), 6.79-6.73 (m, 2H), 6.14-6.10 (m, 1H), 4.24 (s, 4H), 3.46 (s, 3H); LCMS: purity: 96%; MS (m/e): 327 (MH$^+$).

N4-(3,4-Ethylenedioxyphenyl)-5-fluoro-N-4-methyl-2-(5-methyl-2-thienyl)-4-pyrimidineamine (Compound 33): $^1$H NMR (CDCl$_3$): δ 7.86 (d, J=5.7 Hz, 1H), 7.59 (bs, 1H), 6.76 (d, J=8.4 Hz, 1H), 6.71-6.64 (m, 2H), 6.62 (dd, J=2.1 and 8.4 Hz, 1H), 4.20 (s, 4H), 3.42 (s, 3H), 2.45 (s, 3H); LCMS: purity: 96%; MS (m/e): 358 (MH$^+$).

N4-(3,4-Ethylenedioxyphenyl)-5-fluoro-N-4-methyl-2-(4-methyl-3-thienyl)-4-pyrimidineamine (Compound 34): $^1$H NMR (CDCl$_3$): δ 8.10 (d, J=3.3 Hz, 1H), 8.04 (dd, J=1.2 and 5.4 Hz, 1H), 7.00-6.96 (m, 1H), 6.85 (dd, J=0.9 and 8.4 Hz, 1H), 6.78-6.70 (m, 2H), 4.28 (s, 4H), 3.51 (s, 3H), 2.59 (s, 3H); LCMS: purity: 94%; MS (m/e): 358 (MH$^+$).

2-(Benzothiophen-2-yl)-N-4-(3,4-ethylenedioxyphenyl)-5-fluoro-N-4-methyl-4-pyrimidineamine (Compound 35): $^1$H NMR (CDCl$_3$): δ 8.08 (s, 1H), 7.95 (d, J=6.0 Hz, 1H), 7.79-7.73 (m, 2H), 7.32-7.25 (m, 2H), 6.78 (d, J=8.7 Hz, 1H), 6.70 (d, J=2.4 Hz, 1H), 6.65 (dd, J=2.1 and 8.7 Hz, 1H), 4.21 (s, 4H), 3.49 (s, 3H); LCMS: purity: 94%; MS (m/e): 394 (MH$^+$).

2-(Benzothiophen-3-yl)-N-4-(3,4-ethylenedioxyphenyl)-5-fluoro-N-4-methyl-4-pyrimidineamine (Compound 36): $^1$H NMR (CDCl$_3$): δ 8.83 (d, J=6.9 Hz, 1H), 8.04 (d, J=5.4 Hz, 1H), 7.80 (d, J=6.6 Hz, 1H), 7.37-7.25 (m, 3H), 6.81 (d, J=8.4 Hz, 1H), 6.72 (d, J=2.1 Hz, 1H), 6.67 (dd, J=2.7 and 8.4 Hz, 1H), 4.23 (s, 4H), 3.54 (s, 3H); LCMS: purity: 99%; MS (m/e): 394 (MH$^+$).

2-(5-Chloro-2-thienyl)-N-4-(3,4-ethylenedioxyphenyl)-5-fluoro-N-4-methyl-4-pyrimidineamine (Compound 37): $^1$H NMR (CDCl$_3$): δ 7.86 (d, J=5.7 Hz, 1H), 7.53 (d, J=3.9 Hz, 1H), 6.83 (d, J=3.9 Hz, 1H), 6.77 (d, J=8.4 Hz, 1H), 6.67 (d, J=2.7 Hz, 1H), 6.62 (dd, J=2.4 and 8.7 Hz, 1H), 4.20 (s, 4H), 3.41 (s, 3H); LCMS: purity: 97%; MS (m/e): 379 (MH$^+$).

2-(Benzofuran-2-yl)-N-4-(3,4-ethylenedioxyphenyl)-5-fluoro-N-4-methyl-4-pyrimidineamine (Compound 38): $^1$H NMR (CDCl$_3$): δ 8.02 (d, J=5.4 Hz, 1H), 7.61-7.49 (m, 3H), 7.28 (dt, J=0.9 and 8.4 Hz, 1H), 7.21-7.16 (m, 1H), 6.79 (d, J=8.7 Hz, 1H), 6.70 (d, J=2.4 Hz, 1H), 6.65 (dd, J=2.7 and 8.7 Hz, 1H), 4.21 (s, 4H), 3.50 (s, 3H); LCMS: purity: 98%; MS (m/e): 378 (MH$^+$).

5.1.4 Synthesis of N4-(3,4-ethylenedioxyphenyl)-5-fluoro-N-4-methyl-2-(2-methylaminomethylenethien-3-yl)-4-pyrimidineamine (Compound 40) via Reductive Animation

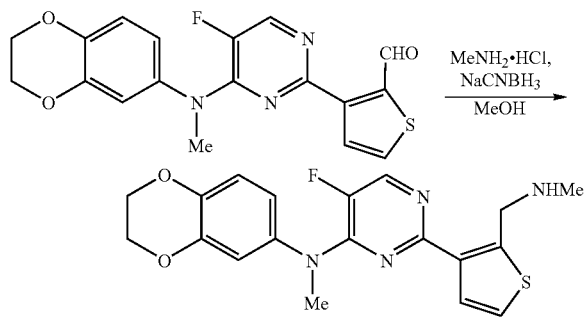

N4-(3,4-Ethylenedioxyphenyl)-5-fluoro-2-(2-formylthien-3-yl)-N-4-methyl-4-pyrimidineamine (Compound 39; 13 mg, 0.037 mmol), methylamine hydrogen chloride salt (13 mg, 0.19 mmol), and sodium cyanoborohydride (20 mg, 0.32 mmol) were combined in methanol (1.5 mL) and stirred at room temperature for 2 h. The reaction mixture was diluted with H$_2$O (10 mL) and extracted with ether. The combined ether extracts were washed with brine, dried over anhydrous magnesium sulfate, and concentrated to give N4-(3,4-ethylenedioxyphenyl)-5-fluoro-N-4-methyl-2-(2-methylaminomethylenethien-3-yl)-4-pyrimidineamine (Compound 40). $^1$H NMR (CDCl$_3$): δ 7.95 (d, J=5.4 Hz, 1H), 7.67 (d, J=5.4 Hz, 1H), 7.11 (d, J=5.4 Hz, 1H), 6.78 (d, J=8.4 Hz, 1H), 6.68 (d, J=2.4 Hz, 1H), 6.63 (dd, J=2.7 and 8.4 Hz, 1H), 4.24-4.17 (m, 7H), 3.44 (s, 3H), 2.45 (s, 3H); LCMS: purity: 89%; MS (m/e): 387 (MH$^+$).

5.1.5 Synthesis of N4-(3,4-Ethylenedioxyphenyl)-5-fluoro-N-4-methyl-2-[(2-(4-methylpiperizin-1-ylmethylene)-3-thienyl]-4-pyrimidineamine (Compound 42)

The synthesis was performed using the above reductive amination procedure with 4-methylpiperazine and sodium cyanoborohydride to afford N4-(3,4-ethylenedioxyphenyl)-5-fluoro-N-4-methyl-2-[(2-(4-methylpiperizin-1-ylmethylene)-3-thienyl]-4-pyrimidineamine (Compound 42). $^1$H NMR (CDCl$_3$): δ 7.96 (d, J=5.4 Hz, 1H), 7.56 (d, J=5.4 Hz, 1H), 7.07 (d, J=5.1 Hz, 1H), 6.77 (d, J=8.1 Hz, 1H), 6.67 (d, J=2.4 Hz, 1H), 6.62 (dd, J=2.4 and 8.4 Hz, 1H), 4.20 (s, 4H), 4.14 (s, 2H), 3.41 (s, 3H), 2.68-2.52 (m, 4H), 2.38-2.50 (m, 4H), 2.26 (s, 3H); LCMS: purity: 95%; MS (m/e): 456 (MH$^+$).

5.1.6 Synthesis of N4-(3,4-ethylenedioxyphenyl)-5-fluoro-N-4-methyl-2-(1-oxide-3-thienyl)-4-pyrimidineamine (Compound 41)

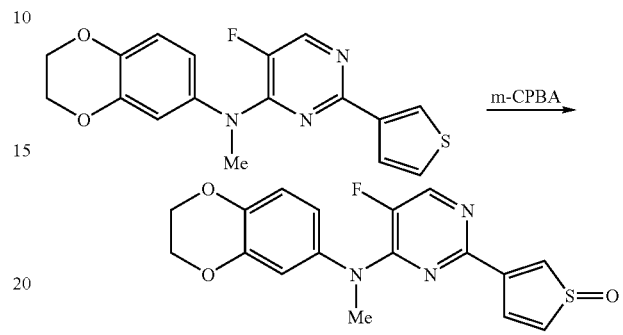

A mixture of N4-(3,4-ethylenedioxyphenyl)-5-fluoro-2-(3-thienyl)-N-4-methyl-4-pyrimidineamine (25 mg, 0.072 mmol) and meta-chloro[erbenzoic acid (m-CPBA, 77% maximum, 100 mg) in 1,2-dichloroethane (1.0 mL) was stirred at RT for 48 h. The reaction mixture was diluted with dichloromethane and saturated aqueous NaHCO$_3$. The organic phase was dried over anhydrous magnesium sulfate and concentrated in vacuo to give brown oil. The product was purified by chromatography (C18, eluted with mixture of acetonitrile and water) to give N4-(3,4-ethylenedioxyphenyl)-5-fluoro-N-4-methyl-2-(1-oxide-3-thienyl)-4-pyrimidineamine (Compound 41). $^1$H NMR (CDCl$_3$): δ 9.31 (d, J=2.4 Hz, 1H), 8.14 (d, J=6.6 Hz, 1H), 7.96 (dd, J=0.9 and 5.1 Hz, 1H), 7.35 (dd, J=3.0 and 5.1 Hz, 1H), 6.87 (d, J=8.7 Hz, 1H), 6.75 (d, J=2.7 Hz, 1H), 6.70 (dd, J=2.7 and 8.7 Hz, 1H), 4.29 (s, 4H), 3.54 (s, 3H); LCMS: purity: 99%; MS (m/e): 360 (MH$^+$).

5.2 Biological Activity

Various exemplary 5-fluoro-4-pyrmidineamine compounds (illustrated in TABLE 1, infra) were synthesized as described herein and tested for their ability to inhibit A549 (lung carcinoma), DLD-1 (colorectal adenocarcinoma), H1299 (non small cell lung carcinoma), HCT116 (colorectal carcinoma), HELA (cervical adenocarcinoma) and/or U2OS (bone osterosarcoma) cells in vitro. Their activities are reported in TABLE 1. In TABLE 1, a value of "+" means the compound exhibited an IC$_{50}$ of ≦20 μM; a value of "++" means the compound exhibited an IC$_{50}$ of ≦10 μM; and a value of "+++" means the compound exhibited an IC$_{50}$ of ≦1 μM. A value of "−" means the compound exhibited an IC$_{50}$ value of >20 μM. A blank indicates the particular compound was tested in that assay.

Compound 1 was tested against the following additional cell lines: ACHN (renal cell adenocarcimona), JAR (placental choriocarcinoma), MCF7 (estrogen-dependent breast adenocarcinoma), MDA-MB-231 (estrogen independent breast adenocarcinoma), SKMEL28 (human melanoma) and SKMEL5 (human melanoma). In all cases, the IC$_{50}$ was less than 1 μM.

Compound 25 was tested against the following cell lines in a 9-point anti-proliferation assay: A549, Colo205 (colorectal adenocarcinoma), HCT116 and Miapaca2 (pancreatic carcinoma) The IC$_{50}$ was less than 1 μM against all three cell lines

TABLE 1

The compounds have the general structure: a 5-fluoropyrimidine bearing R² at the 2-position and an N(R⁴')-aryl group at the 4-position, where the aryl group bears R⁸, R⁹, R¹⁰ substituents.

| Compound | R² | R⁴' | R⁸ | R⁹ | R¹⁰ | A549 | H1299 | DLD-1 | HCT116 | HELA | U2OS |
|---|---|---|---|---|---|---|---|---|---|---|---|
| 1 | Cl | Me | H | —O—CH₂CH₂—O— | OMe | +++ | +++ | | +++ | +++ | +++ |
| 2 | Cl | Me | H | —O—CH₂CH₂—O— | OMe | +++ | +++ | | | | |
| 3 | Cl | —CH₂C(O)OMe | H | —O—CH₂CH₂—O— | Cl | ++ | ++ | | | | |
| 4 | Cl | Me | H | —OC(Me)₂C(O)OEt | Cl | ++ | ++ | | | | |
| 5 | Cl | Me | Cl | OMe | Cl | ++ | ++ | | | | |
| 6 | Cl | Me | H | Cl | OMe | — | — | | | | |
| 7 | Cl | Me | H | OMe | Cl | ++ | ++ | | | | |
| 8 | Cl | Me | H | —C(Me)₂C(O)NHMe | Cl | — | — | | | | |
| 9 | Cl | n-Pr | H | OMe | Cl | ++ | ++ | | | | |
| 10 | Cl | Me | OMe | OMe | OMe | — | — | | | | |
| 11 | Cl | Me | Me | Cl | Me | — | — | | | | |
| 12 | Cl | Me | Cl | H | OMe | ++ | ++ | | | | |
| 13 | Cl | Me | H | OMe | Cl | ++ | ++ | | | | |
| 14 | Cl | Me | H | Cl | CF₃ | — | — | | | | |
| 15 | OMe | Me | H | —O—CH₂CH₂—O— | | ++ | ++ | | | | |
| 18 | Ph | Me | H | —O—CH₂CH₂—O— | | +++ | +++ | | | | |

TABLE 1-continued

| Compound | R² | R⁴' | R⁸ | R⁹ | R¹⁰ | A549 | H1299 | DLD-1 | HCT116 | HELA | U2OS |
|---|---|---|---|---|---|---|---|---|---|---|---|
| 19 | OH-phenyl | Me | H | —O—CH₂CH₂—O— | | ++ | ++ | | | | |
| 20 | dimethoxyphenyl | Me | H | —O—CH₂CH₂—O— | | − | − | − | − | − | − |
| 21 | benzodioxole | Me | H | —O—CH₂CH₂—O— | | ++ | ++ | + | + | + | + |
| 22 | furyl | Me | H | —O—CH₂CH₂—O— | | +++ | +++ | ++ | ++ | ++ | ++ |
| 23 | NH₂-phenyl | Me | H | —O—CH₂CH₂—O— | | +++ | +++ | ++ | ++ | ++ | ++ |

TABLE 1-continued

| Compound | R² | R⁴' | R⁸ | R⁹ | R¹⁰ | A549 | H1299 | DLD-1 | HCT116 | HELA | U2OS |
|---|---|---|---|---|---|---|---|---|---|---|---|
| 25 | thiophen-3-yl | Me | H | —O—CH₂CH₂—O— | | +++ | +++ | +++ | +++ | +++ | +++ |
| 26 | furan-3-yl | Me | H | —OCH₂CH₂—O— | | +++ | +++ | +++ | +++ | +++ | +++ |
| 27 | pyridin-3-yl | Me | H | —OCH₂CH₂—O— | | ++ | ++ | | | | |
| 28 | pyridin-4-yl | Me | H | —OCH₂CH₂—O— | | +++ | +++ | | | | |
| 29 | 3,5-dimethylisoxazol-4-yl | Me | H | —OCH₂CH₂—O— | | ++ | ++ | | | | |

TABLE 1-continued

| Compound | R² | R⁴' | R⁸ | R⁹ | R¹⁰ | A549 | H1299 | DLD-1 | HCT116 | HELA | U2OS |
|---|---|---|---|---|---|---|---|---|---|---|---|
| 30 | thiazol-2-yl | Me | H | —OCH₂CH₂—O— | | ++ | ++ | | | | |
| 31 | 1H-pyrrol-2-yl | Me | H | —OCH₂CH₂—O— | | +++ | +++ | +++ | +++ | +++ | +++ |
| 33 | 5-methylthien-2-yl | Me | H | —OCH₂CH₂—O— | | ++ | ++ | | | | |
| 34 | 4-methylthien-3-yl | Me | H | —OCH₂CH₂—O— | | +++ | +++ | | | | |
| 35 | benzothien-2-yl | Me | H | —OCH₂CH₂—O— | | − | − | | | | |

TABLE 1-continued

| Compound | R² | R⁴' | R⁸ | R⁹ | R¹⁰ | A549 | H1299 | DLD-1 | HCT116 | HELA | U2OS |
|---|---|---|---|---|---|---|---|---|---|---|---|
| 36 | benzothiophen-3-yl | Me | H | —OCH₂CH₂—O— | | − | − | | | | |
| 37 | 5-chlorothiophen-2-yl | Me | H | —OCH₂CH₂—O— | | − | + | | | | |
| 38 | benzofuran-2-yl | Me | H | —OCH₂CH₂—O— | | | | | | | |
| 39 | 3-formylthiophen-2-yl | Me | H | —OCH₂CH₂—O— | | +++ | +++ | | | | |

TABLE 1-continued

| Compound | R² | R⁴' | R⁸ | R⁹ | R¹⁰ | A549 | H1299 | DLD-1 | HCT116 | HELA | U2OS |
|---|---|---|---|---|---|---|---|---|---|---|---|
| 40 | (methylaminomethyl-thiophene) | Me | H | | —OCH₂CH₂O— | ++ | ++ | | | | |
| 41 | (thiophene S-oxide) | Me | H | | —OCH₂CH₂O— | ++ | ++ | | | | |
| 42 | (N-methylpiperazinylmethyl-thiophene) | Me | H | | —OCH₂CH₂O— | | | | | | |

Although the foregoing inventions have been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated by reference into the application for all purposes.

What is claimed is:

1. A compound according to structural formula (I):

or a salt, N- or S-oxide therof, wherein:
   $R^2$ is selected from hydroxy, lower alkoxy optionally substituted with one or more of the same or different $R^d$ groups, $C_5$-$C_{14}$ aryloxy optionally substituted with one or more of the same or different $R^d$ groups, a lower alkyl-, aryl- or arylalkyl-sulfonate optionally substituted with one or more of the same or different $R^d$ groups, $C_5$-$C_{14}$ aryl optionally substituted with one or more of the same or different $R^d$ groups, $C_6$-$C_{20}$ arylalkyl optionally substituted with one or more of the same or different $R^d$ groups, 5-14-membered heteroaryl optionally substituted with one or more of the same or different $R^d$ groups and 6-20 membered heteroarylalkyl optionally substituted with one or more of the same or different $R^d$ groups;
   $R^{4'}$ is a lower alkyl optionally substituted with one or more of the same or different $R^e$ groups;
   $R^5$ is —C(O)$R^a$, —C(O)O$R^a$, —C(O)N$R^c R^c$, —CH$_2$OH, halo, nitro, cyano, or trifluoromethyl;
   $R^8$ is selected from hydrogen and halo;
   $R^9$ is selected from hydroxy, lower alkoxy optionally substituted with one or more of the same or different $R^e$ groups, trifluoromethoxy and halo, or, alternatively, $R^9$ is taken together with $R^{10}$ to form a heteroalkylene bridge of the formula —O—(C$R^a R^a$)$_n$—O—, where n is 1, 2 or 3;
   $R^{10}$ is selected from lower alkyl, lower alkoxy and halo or, alternatively, $R^{10}$ is taken together with $R^9$ to form a heteroalkylene bridge of the formula —O—(C$R^a R^a$)$_n$—O—, where n is 1, 2 or 3;
   each $R^a$ is, independently of the others, selected from hydrogen and lower alkyl;
   each $R^c$ is, independently of the other, selected from hydrogen and lower alkyl, or alternatively, two $R^c$ groups bonded to the same nitrogen atom may be taken together with that atom to form a 5 to 7-membered heterocyclic ring that may optionally include from 1 to 4 of the same or different additional heteroatoms selected from O, N and S, and which may further optionally include a lower alkyl substituent at one or more available carbon and/or nitrogen atoms;
   each $R^d$ is, independently of the others, selected from a water-solubilizing group, hydroxy, lower alkoxy, and —C(O)$R^a$ and —(CH$_2$)$_m$N$R^c R^c$, where m is 0, 1, 2 or 3; and
   $R^e$ is selected from —N$R^c R^c$, —C(O)O$R^a$ and —C(O)N$R^c R^c$,
   wherein the water-solubilizing group is where Y is selected from CH and N and Z is selected from CH$_2$, O, S, NH, N—(CH$_2$)$_y$—$R^a$, N—(CH$_2$)$_y$—C(O)$R^a$, N—(CH$_2$)$_y$—C(O)O$R^a$, N—(CH$_2$)$_y$—S(O)$_2 R^a$, N—CH$_2$—S(O)$_2$O$R^a$ and N—(CH$_2$)$_y$—C(O)N$R^c R^c$, provided that Y and Z are not both simultaneously CH and CH$_2$, respectively, and y is an integer from 0 to 6.

2. The compound of claim 1 in which $R^{4'}$ is a $C_1$-$C_3$ unsubstituted n-alkynyl.

3. The compound of claim 1 in which $R^5$ is fluoro.

4. The compound of claim 1 in which $R^8$ is hydrogen and $R^9$ and $R^{10}$ are taken together to form a heteroalkylene bridge of the formula —O—CH$_2$CH$_2$—O—.

5. The compound of claim 1 in which $R^2$ is phenyl optionally substituted with one or more of the same or different $R^d$ groups.

6. The compound of claim 5 in which the phenyl is unsubstituted.

7. The compound of claim 5 in which the phenyl is mono-substituted at the 3-position.

8. The compound of claim 5 in which the phenyl is di-substituted at the 3- and 4-positions.

9. The compound of claim 8 in which the substituents at the 3- and 4-positions are taken together to form a heteroalkylene bridge of the formula —O—(CH$_2$)$_z$—O—, where z is an integer from 1 to 3.

10. The compound of claim 5 in which the phenyl is tri-substituted at the 2-, 3- and 4-positions.

11. The compound of claim 1 in which $R^2$ is heteroaryl optionally substituted with one or more of the same or different $R^d$ groups.

12. A composition comprising a 4-pyrimidinediamine compound and a pharmaceutically acceptable carrier, excipient and/or diluent, wherein said pyrimidineamine compound has the structural formula (I):

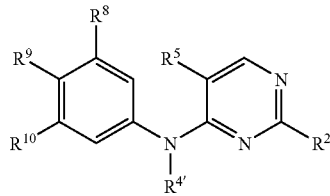
(I)

or a salt, N- or S-oxide thereof, wherein:

$R^2$ is selected from hydroxy, lower alkoxy optionally substituted with one or more of the same or different $R^d$ groups, $C_5$-$C_{14}$ aryloxy optionally substituted with one or more of the same or different $R^d$ groups, lower alkyl-, aryl- or arylalkyl-sulfonate optionally substituted with one or more of the same or different $R^d$ groups, halo, $C_5$-$C_{14}$ aryl optionally substituted with one or more of the same or different $R^d$ groups, $C_6$-$C_{20}$ arylalkyl optionally substituted with one or more of the same or different $R^d$ groups, 5-14-membered heteroaryl optionally substituted with one or more of the same or different $R^d$ groups and 6-20 membered heteroarylalkyl optionally substituted with one or more of the same or different $R^d$ groups;

$R^{4'}$ is a lower alkyl optionally substituted with one or more of the same or different $R^e$ groups;

$R^5$ is —$C(O)R^a$, —$C(O)OR^a$, —$C(O)NR^cR^c$, —$CH_2OH$, halo, nitro, cyano, or trifluoromethyl;

$R^8$ is selected from hydrogen and halo;

$R^9$ is selected from hydroxy, lower alkoxy optionally substituted with one or more of the same or different $R^e$ groups, trifluoromethoxy and halo, or, alternatively, $R^9$ is taken together with $R^{10}$ to form a heteroalkylene bridge of the formula —O—$(CR^aR^a)_n$—O—, where n is 1, 2 or 3;

$R^{10}$ is selected from lower alkyl, lower alkoxy and halo or, alternatively, $R^{10}$ is taken together with $R^9$ to form a heteroalkylene bridge of the formula —O—$(CR^aR^a)_n$—O—, where n is 1, 2 or 3;

each $R^a$ is, independently of the others, selected from hydrogen and lower alkyl;

each $R^c$ is, independently of the other, selected from hydrogen and lower alkyl, or alternatively, two $R^c$ groups bonded to the same nitrogen atom may be taken together with that atom to form a 5 to 7-membered heterocyclic ring that may optionally include from 1 to 4 of the same or different additional heteroatoms selected from O, N and S, and which may further optionally include a lower alkyl substituent at one or more available carbon and/or nitrogen atoms;

each $R^d$ is, independently of the others, selected from a water-solubilizing group, hydroxy, lower alkoxy, and —$C(O)R^a$ and —$(CH_2)_mNR^cR^c$, where m is 0, 1, 2 or 3; and $R^e$ is selected from —$NR^cR^c$, —$C(O)OR^a$ and —$C(O)NR^cR^c$ wherein the water-solubilizing group is

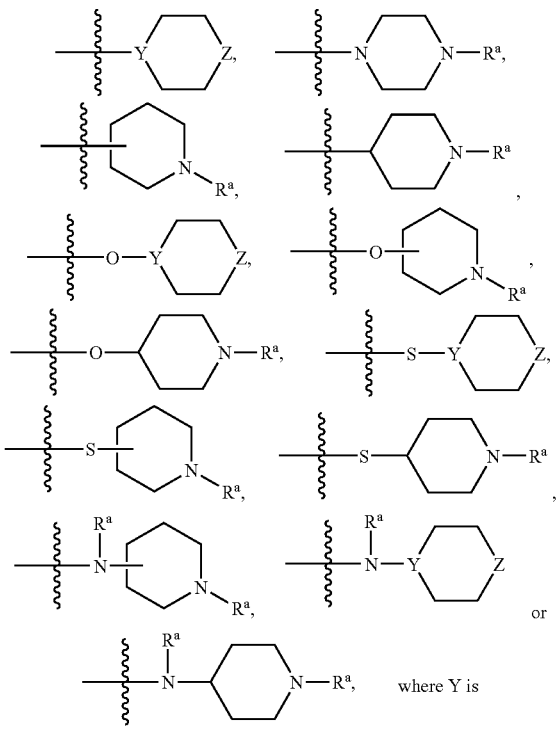

selected from CH and N and Z is selected from $CH_2$, O, S, NH, N—$(CH_2)_y$—$R^a$, N—$(CH_2)_y$—$C(O)R^a$, N—$(CH_2)_y$—$C(O)OR^a$, N—$(CH_2)_y$—$S(O)_2R^a$, N—$CH_2$—$S(O)_2OR^a$ and N—$(CH_2)_y$—$C(O)NR^cR^c$, provided that Y and Z are not both simultaneously CH and $CH_2$, respectively, and y is an integer from 0 to 6.

13. The composition of claim 12 which is packaged in unit dosage form.

14. A method of inhibiting proliferation of a breast, colon, pancreatic, lung, bone, or renal tumor cell comprising contacting the cell with an amount of a compound according to structural formula (I) effective to inhibit its proliferation:

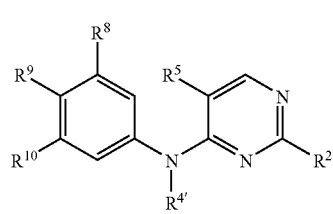
(I)

or a salt, N- or S-oxide thereof, wherein:

$R^2$ is selected from hydroxy, lower alkoxy optionally substituted with one or more of the same or different $R^d$ groups, $C_5$-$C_{14}$ aryloxy optionally substituted with one or more of the same or different $R^d$ groups, lower alkyl-, aryl- or arylalkyl-sulfonate optionally substituted with one or more of the same or different $R^d$ groups, halo, $C_5$-$C_{14}$ aryl optionally substituted with one or more of the same or different $R^d$ groups, $C_6$-$C_{20}$ arylalkyl optionally substituted with one or more of the same or different $R^d$ groups, 5-14-membered heteroarylalkyl optionally substituted with one or more of the same or different $R^d$ groups and 6-20 membered heteroarylalkyl optionally substituted with one or more of the same or different $R^d$ groups;

$R^{4'}$ is a lower alkyl optionally substituted with one or more of the same or different $R^e$ groups;

$R^5$ is —C(O)$R^a$, —C(O)O$R^a$, —C(O)N$R^c R^c$, —CH$_2$OH, halo, nitro, cyano, or trifluoromethyl;

$R^8$ is selected from hydrogen and halo;

$R^9$ is selected from hydroxy, lower alkoxy optionally substituted with one or more of the same or different $R^e$ groups, trifluoromethoxy and halo, or, alternatively, $R^9$ is taken together with $R^{10}$ to form a heteroalkylene bridge of the formula —O—(C$R^a R^a$)$_n$—O—, where n is 1, 2 or 3;

$R^{10}$ is selected from lower alkyl, lower alkoxy and halo or, alternatively, $R^{10}$ is taken together with $R^9$ to form a heteroalkylene bridge of the formula —O—(C$R^a R^a$)$_n$—O—, where n is 1, 2 or 3;

each $R^a$ is, independently of the others, selected from hydrogen and lower alkyl;

each $R^c$ is, independently of the other, selected from hydrogen and lower alkyl, or alternatively, two $R^c$ groups bonded to the same nitrogen atom may be taken together with that atom to form a 5 to 7-membered heterocyclic ring that may optionally include from 1 to 4 of the same or different additional heteroatoms selected from O, N and S, and which may further optionally include a lower alkyl substituent at one or more available carbon and/or nitrogen atoms;

each $R^d$ is, independently of the others, selected from a water-solubilizing group, hydroxy, lower alkoxy, and —C(O)$R^a$ and —(CH$_2$)$_m$N$R^c R^c$, where m is 0, 1, 2 or 3; and $R^e$ is selected from —N$R^c R^c$, —C(O)O$R^a$ and —C(O)N$R^c R^c$ wherein the water-solubilizing group is

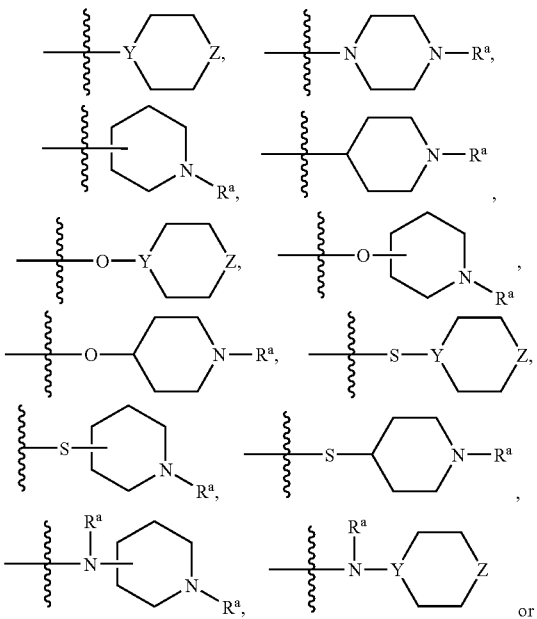

or

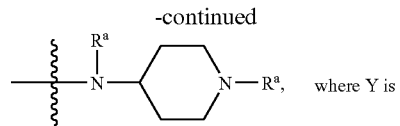

where Y is selected from CH and N and Z is selected from CH$_2$, O, S, NH, N—(CH$_2$)$_y$—$R^a$, N—(CH$_2$)$_y$—C(O)$R^a$, N—(CH$_2$)$_y$—C(O)O$R^a$, N—(CH$_2$)$_y$—S(O)$_2 R^a$, N—CH$_2$—S(O)$_2$O$R^a$ and N—(CH$_2$)$_y$—C(O)N$R^c R^c$, provided that Y and Z are not both simultaneously CH and CH$_2$, respectively, and y is an integer from 0 to 6.

15. A method of treating a cancer selected from breast cancer, colon cancer, pancreatic cancer, lung cancer, renal cancer, and bone cancer, comprising administering to a subject in need thereof an amount of a compound according to structural formula (I) effect to treat the proliferative disease:

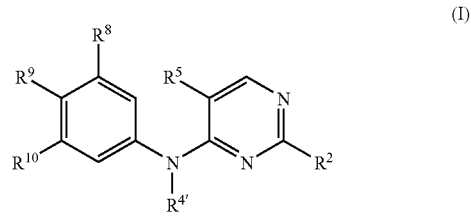

(I)

or a salt, N- or S-oxides thereof, wherein:

$R^2$ is selected from hydroxy, lower alkoxy optionally substituted with one or more of the same or different $R^d$ groups, C$_5$-C$_{14}$ aryloxy optionally substituted with one or more of the same or different $R^d$ groups, lower alkyl-, aryl- or arylalkyl-sulfonate optionally substituted with one or more of the same or different $R^d$ groups, halo, C$_5$-C$_{14}$ aryl optionally substituted with one or more of the same or different $R^d$ groups, C$_6$-C$_{20}$ arylalkyl optionally substituted with one or more of the same or different $R^d$ groups, 5-14-membered heteroaryl optionally substituted with one or more of the same or different $R^d$ groups and 6-20 membered heteroarylalkyl optionally substituted with one or more of the same or different $R^d$ groups;

$R^{4'}$ is a lower alkyl optionally substituted with one or more of the same or different $R^e$ groups;

$R^5$ is —C(O)$R^a$, —C(O)O$R^a$, —C(O)N$R^c R^c$, —CH$_2$OH, halo, nitro, cyano, or trifluoromethyl;

$R^8$ is selected from hydrogen and halo;

$R^9$ is selected from hydroxy, lower alkoxy optionally substituted with one or more of the same or different $R^e$ groups, trifluoromethoxy and halo, or, alternatively, $R^9$ is taken together with $R^{10}$ to form a heteroalkylene bridge of the formula —O—(C$R^a R^a$)$_n$—O—, where n is 1, 2 or 3;

$R^{10}$ is selected from lower alkyl, lower alkoxy and halo or, alternatively, $R^{10}$ is taken together with $R^9$ to form a heteroalkylene bridge of the formula —O—(C$R^a R^a$), —O—, where n is 1, 2 or 3;

each $R^a$ is, independently of the others, selected from hydrogen and lower alkyl;

each $R^c$ is, independently of the other, selected from hydrogen and lower alkyl, or alternatively, two $R^c$ groups bonded to the same nitrogen atom may be taken together with that atom to form a 5 to 7-membered heterocyclic ring that may optionally include from 1 to 4 of the same or different additional heteroatoms selected from O, N and S, and which may further optionally include a lower alkyl substituent at one or more available carbon and/or nitrogen atoms;

each $R^d$ is, independently of the others, selected from a water-solubilizing group, hydroxy, lower alkoxy, and —C(O)$R^a$ and —(CH$_2$)$_m$NR$^c$R$^c$, where m is 0, 1, 2 or 3; and $R^e$ is selected from —NR$^c$R$^c$, —C(O)OR$^a$ and —C(O)NR$^c$R$^c$.

wherein the water-solubilizing group is

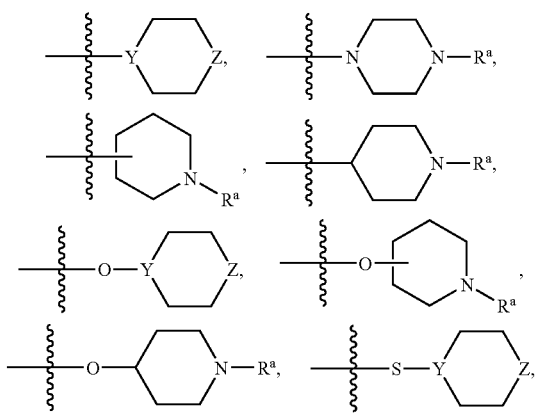

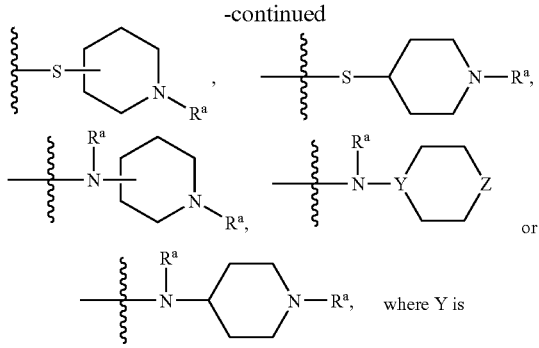

selected from CH and N and Z is selected from CH$_2$, O, S, NH, N—(CH$_2$)$_y$—C(O)R$^a$, N—(CH$_2$)$_y$—C(O)OR$^a$, N—(CH$_2$)R$^a$, N—(CH$_2$)$_y$—S(O)$_2$OR$^a$ and N—(CH$_2$)$_y$—C(O)NR$^c$R$^c$, provided that Y and Z are not both simultaneously CH and CH$_2$, respectively, and y is an integer from 0 to 6.

16. The method of claim 15 in which the cancer is a metastatic tumor.

17. The method of claim 15 in which the compound is administered in the form of a pharmaceutical composition.

18. The method of claim 15 in which the compound is administered orally.

19. The method of claim 15 in which the compound is administered intravenously.

20. The method of claim 15 in which the subject is a human.

* * * * *